US007052900B2

(12) United States Patent
Muller et al.

(10) Patent No.: US 7,052,900 B2
(45) Date of Patent: May 30, 2006

(54) SACCHAROMYCES CEREVISIAE YEAST STRAIN WITH FUNCTIONAL EXPRESSION OF A GLUT TRANSPORTER

(75) Inventors: Gunter Muller, Sulzbach a. Ts. (DE);
Klaus-Peter Koller, Bad Soden (DE);
Eckhard Boles, Dusseldorf (DE);
Roman Wieczorke, Dusseldorf (DE);
Silke Dlugai, Dusseldorf (DE)

(73) Assignee: sanofi-aventis Pharma Deutschland GmbH, Frankfurt am Main (DE)

(*) Notice: Subject to any disclaimer, the term of this patent is extended or adjusted under 35 U.S.C. 154(b) by 318 days.

(21) Appl. No.: 10/067,449

(22) Filed: Feb. 5, 2002

(65) Prior Publication Data

US 2003/0166258 A1 Sep. 4, 2003

(30) Foreign Application Priority Data

Feb. 14, 2001 (DE) ............................... 101 06 718

(51) Int. Cl.
*C12N 1/16* (2006.01)
*C12N 15/00* (2006.01)
*C12N 15/74* (2006.01)
*C12P 21/00* (2006.01)

(52) U.S. Cl. ................. 435/254.21; 435/483; 435/440; 435/71.1

(58) Field of Classification Search ................. 435/243, 435/254.11, 254.21, 320.1, 255.2, 471, 483, 435/23.1; 536/23.1
See application file for complete search history.

(56) References Cited

OTHER PUBLICATIONS

Kasahara et al., Characterization of rat Glut4 glucose transporter expressed in the yeast Saccharomyces cerevisiae: comparison with Glut 1 glucose transporter, Biochimiça et Biophysica Acta, 1997, pp. 111-119.*

R. Wieczorke et al., Concurrent knock-out of at least 20 transporter genes is required to block update of hexoses in Saccharomyces cerevisiae, FEBS Lett. vol. 464, (1999), pp. 123-128.

Kruckberg et al., The HXT2 Gene of Saccharomyces cerevisiae Is Required for High-Affinity Glucose Transport, Molecular and Cellular Biology, vol. 10, No. 11, Nov. 1990, pp. 5903-5913.

Fukumoto et al., Cloning and Characterization of the Major Insulin-responsive Glucose Transporter Expressed in Human Skeletal Muscle and Other Insulin-responsive Tissues, Journal of Bio. Chem., vol. 264, No. 15, May 15, 1989, pp. 7776-7779.

Bimbaum et al., Cloning and characterization of an cDNA encoding the rat brain glucose-transporter protein, Proc. Natl. Acad Sci. USA vol. 83, Aug. 1986, pp. 5784-5788.

Asano, et al., The Role of N-Glycosylation of GLUT1 for Glucose Transport Activity, Journal of Biological Chemistry, vol. 286, No. 36, Dec. 15, 1991, pp. 24632-24636.

Kasahara et al., Expression of the rat GLUT1 glucose transporter in the yeast Saccharomyces cerevisiae, Biochem J. vol. 315, 1996, pp. 177-182.

Kasahara et al., Studies on the Glut Family Transporters: Use of the Yeast Expression System, International Symposium Kyushu Univ., 1997, pp. 201-212.

Kasahara et al., Tryptophan 388 in Putative Transmembrane Segment 10 of the Rat Glucose Transpoter Glut1 Is Essential for Glucose Transport, Journal of Biological Chemistry, vol. 273, No. 44, Oct. 30, 1998, pp. 29113-29117.

GenBank Accession No. Y17803, publicly available Jul. 13, 2001.

GenBank Accession No. M23384, publicly available Jun. 12, 1993.

GenBank Accession No. M13979, publicly available Apr. 27, 1993.

GenBank Accession No. M20653, publicly available Jun. 12, 1997.

GenBank Accession No. P17809, publicly available Jun. 15, 2002.

GenBank Accession No. P11167, publicly available Jun. 15, 2002.

(Continued)

*Primary Examiner*—Celian Qian
*Assistant Examiner*—Jennifer Dunston
(74) *Attorney, Agent, or Firm*—Bell, Boyd & Lloyd LLC

(57) ABSTRACT

The invention relates to a strain of the yeast Saccharomyces cerevisiae which, owing to deletion of the genomic sequences, no longer synthesizes hexose transporters and, as a consequence, can no longer grow on substrates with hexoses as the only carbon source, and whose ability of growing on a substrate with a hexose as the only carbon source is restored when it expresses a GLUT4 gene.

4 Claims, No Drawings

OTHER PUBLICATIONS

GenBank Accession No. P11166, publicly available Sep. 15, 2003
GenBank Accession No. P19357, publicly available Jun. 15, 2002.
GenBank Accession No. P14672, publicly available Jun. 15, 2002.
GenBank Accession No. 14142, publicly available Sep. 15, 2003.
GenBank Accession No. M23382, publicly available Sep. 7, 1994.
GenBank Accession No. D28561, publicly available Jan. 13, 2000.
GenBank Accession No. M20747, publicly available Jan. 6, 1995.

* cited by examiner

SACCHAROMYCES CEREVISIAE YEAST STRAIN WITH FUNCTIONAL EXPRESSION OF A GLUT TRANSPORTER

FOREIGN PRIORITY CLAIM

This application claims the priority under 35 U.S.C. § 119 of German Application No. 101 06 718.6 filed Feb. 14, 2001, which is hereby incorporated by reference herein in its entirety.

The invention relates to a strain of the yeast *Saccharomyces cerevisiae* which, owing to deletion of the genomic sequences, no longer synthesizes hexose transporters and, as a consequence, can no longer grow on substrates with hexoses as the only carbon source, and whose ability of growing on a substrate with a hexose as the only carbon source is restored when it expresses a GLUT4 gene.

Most of the heterotrophic cells transport glucose into the interior of the cell via specific transporter proteins. In the various organisms, different mechanisms which mediate glucose transport have evolved, that is to say proton symport systems, $Na^+$ glucose cotransporters, binding-protein-dependent systems, phosphotransferase systems and systems for facilitated diffusion. In the case of eukaryotes, a glucose transporter family, encoded, in mammals, by the GLUT genes and in *Saccharomyces cerevisiae* by the HXT genes, mediates glucose uptake via facilitated diffusion. These transporters belong to a larger sugar transport superfamily and are characterized by the presence of 12 transmembrane helices and a plurality of conserved amino acid residues and motifs.

Glucose transport in mammals was the focus of a number of studies since the knowledge of the processes is highly important in diseases associated with deficient glucose homeostasis, such as, for example, diabetes mellitus or Fanconi-Bickel syndrome. Eight glucose transporters (GLUT1 to GLUT5, GLUT8, GLUT9/SLC2A9, GLUT9 (GenBank accession No. Y17803)) have so far been identified, all of which contribute to the facilitated uptake of glucose. The key roles of these transporters include the uptake of glucose into a variety of tissues, their storage in the liver, their insulin-dependent uptake into the muscle cells and adipocytes, and glucose measurement by the pancreatic β-cells. GLUT1 mediates the transport of glucose into the erythrocytes and across the blood-brain barrier, but is also expressed in many other tissues, while GLUT4 is limited to insulin-dependent tissue, mainly to muscle and fatty tissue. In these insulin-dependent tissues, controlling the targeting of GLUT4 transporters into intracellular compartments or plasma membrane compartments constitutes an important mechanism for regulating glucose uptake. In the presence of insulin, intracellular GLUT4 is redistributed to the plasma membrane in order to facilitate the uptake of glucose. GLUT1 is also expressed in these insulin-dependent tissues, and its distribution in the cell is also affected by insulin, but to a lesser extent. In addition, the relative efficacy with which GLUT1 or GLUT4 catalyzes the transport of sugar is not only determined by the extent to which each transporter is targeted to the cell surface, but also by their kinetic properties. The fact that different glucose transporter isoforms are coexpressed, and that glucose is metabolized rapidly, has made studies into the role and detailed properties of each glucose transporter isoform in these insulin-dependent tissues a complicated task. Heterologous expression systems such as Xenopus oocytes, tissue culture cells, insect cells and yeast cells have been used to solve these problems. However, it emerged that these systems presented difficulties: too weak an activity of the heterologously expressed transporters, intrinsic glucose transporters in these systems, the intracellular retention of many of the transporters, or indeed the production of inactive transporters.

No organism is known as yet which, besides a heterologous and functional Glut4 glucose transport protein, expresses no further hexose transport protein, in particular intrinsic hexose transport protein. This leads to a series of disadvantages in the search for compounds which are capable of modifying the transport properties of the Glut4 protein. Such compounds would be of considerable interest as components of pharmaceuticals since it is known that Glut4 plays an important role in lowering the glucose concentration in the blood together with insulin and other factors. An organism which expresses a functional Glut4 transport protein would allow the search for compounds which directly affect the Glut4 transporter. The side effects of such compounds would be less pronounced since no signal-factor-mediated side effects would occur. Moreover, handling and providing the material would be greatly facilitated if a yeast strain were available. An object of the invention is therefore to provide a yeast strain which expresses a functional Glut4 protein.

The invention relates to a strain of the yeast *Saccharomyces cerevisiae* which can no longer grow on substrates with hexoses as the only carbon source, and whose ability of growing on a substrate with a hexose as the only carbon source is restored when it expresses a GLUT4 gene. Such a strain can be generated for example by mutating or deleting the relevant genomic sequences. Hexoses are understood as meaning aldoses having 6 carbon atoms, such as glucose, galactose or mannose, and ketoses having 6 carbon atoms, such as fructose or sorbose.

The invention furthermore relates to a strain of the yeast *Saccharomyces cerevisiae* as described above, this strain comprising a GLUT4 gene.

In the yeast *Saccharomyces cerevisiae*, 17 hexose transporters and additionally three maltose transporters are known, which are capable of transporting hexoses into the yeast if they are expressed strongly enough. A strain is known in which all of the transporters which are capable of taking up hexoses have been removed by deletion. This strain now only comprises the two genes MPH2 and MPH3, which are homologous to maltose transport proteins. The two genes MPH2 and MPH3 are repressed when glucose is present in the medium. The generation and characterization of this yeast strain is described in Wieczorke et al., FEBS Lett. 464, 123–128 (1999). This strain is not capable of growing on a substrate with glucose as the only carbon source. Mutants can be selected from this strain which, on the basis of a suitable vector, functionally express Glut1 (strain hxt fgy1-1). If a plasmid vector which carries a GLUT4 gene under the control of a yeast promoter is transformed into the yeast strain hxt fgy1-1, however, only a very small amount of glucose is transported. The functional expression of Glut4 requires further adaptations of this yeast strain to allow a significant glucose transport by means of Glut4. Such yeast strains which take up glucose into the cells by means of a single glucose transporter Glut4 can be isolated on substrates with glucose as the only carbon source. To this end, a yeast strain hxt fgy1-1, which carries a Glut4 gene under the functional control of a yeast promoter, is transformed. These yeast cells which have been transformed in this manner are plated onto a medium which comprises glucose as the only carbon source and are incubated thereon. After a few days incubation at, for example, 30° C., the growth of individual colonies is observed. One of these colonies is isolated. If the yeast plasmid is removed from this colony, no growth takes place on the medium with glucose as the only carbon source. If a yeast vector, which carries a GLUT4 gene under the functional control of a yeast promoter, is transformed into this strain, which now no longer comprises vector plasmid, then this strain regains the ability of growing on a medium with glucose as the only carbon source. The generation of a *Saccharomyces cerevisiae* strain which makes possible the uptake of glucose by means of a Glut4 transporter is described in detail in the examples. This strain expresses no yeast hexose transporters and is capable of taking up hexoses, in particular glucose, into the cell by means of a gene for a Glut4 transporter, for example a gene which has been transformed into this strain. Yeast strains with this characteristic have been deposited under the number DSM 14035, DSM 14036 or DSM 14037 at the Deutsche Sammlung von Mikroorganismen und Zellkulturen GmbH, (DSMZ) in Braunschweig in compliance with the provisions of the Budapest treaty on the international recognition of the deposit of microorganisms for the purposes of patent procedure (Table 1).

In a preferred embodiment of the *Saccharomyces cerevisiae* strain of the present invention, a GLUT4 gene is expressed under the functional control of a yeast expression promoter. The skilled worker is familiar with suitable yeast expression promoters. They are, for example, the SOD1 promoter (superoxide dismutase), ADH promoter (alcohol dehydrogenase), the promoter for the acid phosphatase gene, the HXT2 promoter (glucose transporter 2), the HXT7 promoter (glucose transporter 7), the GAL2 promoter (galactose transporter) and others. For the purpose of expression, the construct, which consists of a yeast expression promoter and a GLUT4 gene, is part of a yeast vector. To carry out the expression, this yeast vector may be present as a self-replicating particle, independently of the yeast genome, or else be stably integrated into the yeast genome. In principle, suitable yeast vectors are all polynucleotide sequences which are capable of multiplication in a yeast. Yeast vectors which can be used in particular are yeast plasmids or yeast artificial chromosomes. Yeast vectors comprise, as a rule, an origin of replication (2µ, ars) for starting replication, and a selection marker which usually consists of an auxotrophism marker or an antibiotic resistance gene. Yeast vectors which are known to the skilled worker are, for example, BM272, pCS19, pEMBCYe23, pFL26, pG6, pNN414, pTV3 or others. In principle, the GLUT4 gene of any species can be expressed. A GLUT4 gene from humans, mice or rats is preferably expressed. The polynucleotide and amino acid sequences for Glut4 are accessible, for example, via the following Genbank accessions: M20747 (cDNA; human), EMBL:D28561 (cDNA; rat), EMBL:M23382 (cDNA; mouse), Swissprot:P14672 (protein; human), Swissprot:P19357 (protein; rat) and Swissprot:P14142 (protein; mouse). The GLUT4 gene is especially preferably expressed by means of the vector YEp4H7-HsGlut4 (SEQ ID No. 9). The GLUT4 gene of this vector is of human origin. The skilled worker is familiar with the generation of a yeast vector comprising a GLUT4 gene for expression in cells. The generation of such a vector is described in the examples. A yeast vector comprising a gene for expression is transformed into the yeast for the gene to be expressed. Methods which are suitable for this purpose are, for example, electroporation or the incubation of competent cells by vector DNA. Transformation is a technique with which the skilled worker is familiar and which serves to introduce foreign DNA, in particular plasmids or vectors, to microorganisms such as yeasts or bacteria. Detailed protocols for the transformation of yeasts, yeast vectors, selection of yeast mutants or the expression of proteins in yeasts are found in the manual "Methods in Yeast Genetics, 1997: A Cold Spring Harbor Laboratory Course Manual; Adams Alison (Edt.); Cold Spring Harbor Laboratory; ISBN:0-87969-508-0", with which the skilled worker is familiar. The evidence that the GLUT4 gene has been expressed in a yeast according to the invention can be provided in particular by Northern blotting, Western blotting, glucose uptake studies and glucose conversion studies or other methods. Northern blotting involves applying isolated RNA of the organism to be studied to a support such as, for example, nitrocellulose and fixing it thereon, followed by incubation of this support, which now contains the RNA of the organism, with radiolabeled or fluorescence-labeled DNA of a GLUT4 polynucleotide sequence. The expression of GLUT4-mRNA in a yeast according to the invention is evidenced by the appearance of black bands. In comparison, no black bands are detected with the RNA of a yeast which is otherwise identical, but has not been transformed with a GLUT4-containing expression vector. Western blotting involves the evidence of the expressed protein after applying a protein extract of the organism to be studied to a membrane support such as nitrocellulose via antibodies. Antibodies for the Glut4 protein can be obtained, for example, from Alpha Diagnostic International, Inc., 5415 Lost Lane, San Antonio, Tex. 78238 USA. The assay systems required for detecting the bound antibody can also be obtained from this supplier. The expressed Glut4 protein is detected in comparison with a yeast strain which is otherwise identical, but does not comprise Glut4 protein. When carrying out glucose uptake studies, radiolabeled glucose is supplied as the only carbon source to the test organism. In contrast with a control strain, which is otherwise identical but does not comprise Glut4 transporter, the yeast with Glut4 as the only glucose transporter transports this radiolabeled glucose into the interior of the cell. Glucose conversion can be tested on nutrient media which comprise glucose as the only carbon source. In contrast to the control, which is otherwise identical but does not comprise Glut4 transporter, the yeast strain with a Glut4 transport protein as the only glucose transporter is capable of growing in the nutrient medium with glucose as the only carbon source. The skilled worker is familiar with these methods which have just been mentioned. Detailed descriptions are found, for example, in "Current Protocols in Molecular Biology; Edited by: F. M. Ausubel, R. Brent, R. E. Kingston, D. M. Moore, J. G. Seidman, J. A. Smith, K. Struhl; published by: John Wiley & Sons; 2000 (currently updated)".

The invention preferably relates to a strain of the yeast *Saccharomyces cerevisiae* wherein a Glut4 gene from humans, mice or rats is expressed.

The invention especially preferably relates to a strain of the yeast *Saccharomyces cerevisiae* wherein a polynucleotide sequence comprising a coding region of a human Glut4 gene is expressed.

In a further preferred embodiment, the invention relates to one or more strains of the yeast *Saccharomyces cerevisiae* deposited, for example, under the Accession No. DSM 14038, DSM 14039 or DSM 14040 at the Deutsche Sammlung von Mikroorganismen und Zellkulturen GmbH, Braunschweig. These strains are listed in table 1. This list contains the information on the yeast strains used, into which the plasmids were transformed, on the plasmids and on the growing conditions for these yeasts.

The present invention also relates to the generation of a strain of the yeast *Saccharomyces cerevisiae* according to the invention, which is obtainable by the following process steps:

a) Providing a yeast which can no longer grow on substrates with hexoses as the only carbon source;

b) Transformation of the yeast of a) by a plasmid encompassing a GLUT4 gene which is under the functional control of a promoter which can be expressed in yeast;

c) Plating a strain which has been transformed in accordance with b) onto a medium comprising a hexose as the only carbon source;

d) Selection of a strain which has been plated in accordance with c) and which grows on this medium and supports the uptake of hexoses by means of the Glut-4 gene.

The invention also relates to growing such a strain.

To provide a yeast in accordance with the invention, a strain of a yeast *Saccharomyces cerevisiae* which can no longer grow on substrates with hexoses as the only carbon source, but whose ability of growing on a substrate with a hexose as the only carbon source is restored when it expresses a Glut4 gene, is isolated in a first step. This can be effected by mutating or deleting the relevant genomic sequences which encode the hexose transporters. Providing the yeast furthermore requires growing this yeast. Growing takes place by standard methods of microbiology in suitable media. Suitable media for growing a yeast are, for example, complete media, in particular YPD medium (yeast extract/peptone/dextrose medium) or selective media and others. The yeast cells are grown in these media, separated from the medium by centrifugation after growing, and, for the purposes of the method, suspended in an aqueous medium comprising, inter alia, buffer substances, salts or other additives, to give an aqueous suspension. The skilled worker will find information on growing yeasts in "Methods in Yeast Genetics, 1997: A Cold Spring Harbor Laboratory Course Manual; Adams Alison (Edt.); Cold Spring Harbor Laboratory; ISBN: 0-87969-508-0", which has already been mentioned above.

In a preferred embodiment of providing a yeast strain as described above, a GLUT4 gene under the functional control of a promoter which can be expressed in yeast is used for the transformation. To carry out the transformation, reference may be made to "Methods in Yeast Genetics", which has already been mentioned above.

A GLUT4 gene which is especially preferably used for the transformation for generating such a yeast strain is a GLUT4 gene from humans, mice or rats. Moreover, a GLUT4 gene which is especially preferably used for the transformation is one which is present in a polynucleotide sequence as shown in SEQ ID No. 9 or 10. SEQ ID No. 9 discloses the polynucleotide sequence of the yeast vector Yep4H7-Hs-GLUT4. This vector comprises a polynucleotide sequence under the functional control of the HXT7 promoter, which polynucleotide sequence encodes the amino acid sequence of the human GLUT4 gene. SEQ ID No. 10 comprises the polynucleotide sequence of vector H2rg4g2. The yeast plasmid H2rg4g2 carries a GLUT4 gene of rats under the functional control of an HXT2 promoter. Functional control of the GLUT4 gene by the promoter means that, by means of the promoter, an mRNA is transcribed which can be translated into a Glut4 protein. As regards the disclosures of the GLUT4 sequences and the methods used, reference may be made to what has already been said above.

The invention furthermore relates to a method of identifying a compound which increases or reduces the amount of a hexose transported by means of a Glut4 protein, with the following process steps:

a) Providing a strain of the yeast *Saccharomyces cerevisiae* according to the present invention which expresses a GLUT4 gene;

b) Determining the amount of a hexose taken up by it;

c) Providing a compound;

d) Contacting a strain of the yeast provided in accordance with a) with a compound provided in accordance with c);

e) Determining the amount of a hexose which is taken up into the yeast strain after contacting in accordance with d);

f) Identifying a compound which increases or reduces the amount of a hexose transported by means of a Glut4 protein by comparing the amount of the hexose taken up into the strain before and after contacting in accordance with d), which is determined in accordance with b) and e).

To provide a yeast according to the invention, a strain of a yeast *Saccharomyces cerevisiae*, which can no longer grow on substrates with hexoses as the only carbon source, but whose ability of growing on a substrate with a hexose as the only carbon source is restored when it expresses a GLUT4 gene, is isolated in a first step. This yeast strain is transformed by means of a yeast vector comprising a GLUT4 gene under the functional control of a yeast promoter. The generation of such a yeast strain is described in the examples. Providing the yeast furthermore requires growing this yeast. Growing takes place by standard methods of microbiology in suitable media. Suitable media for growing a yeast are, for example, complete media, in particular YPD medium (yeast extract/peptone/dextrose medium) or selective media and others. The yeast cells are grown in these media, separated from the medium by centrifugation after growing, and, for the purposes of the method, suspended in an aqueous medium comprising, inter alia, buffer substances, salts or other additives, to give an aqueous suspension. The skilled worker will find information on growing yeasts in "Methods in Yeast Genetics, 1997: A Cold Spring Harbor Laboratory Course Manual; Adams Alison (Edt.); Cold Spring Harbor Laboratory; ISBN: 0-87969-508-0", which has already been mentioned above.

The amount of a hexose which is taken up by a yeast strain provided as has just been described above can be determined by uptake studies with radiolabeled glucose. To this end, a specific amount of yeast cells, for example an amount with a wet weight of 60 mg per ml, is suspended in, for example, 100 µl of a buffer and treated with a defined amount of $^{14}C$— or $^{3}H$—labeled glucose as the only carbon source. The cells are incubated, and defined amounts of the cells are sampled at specific times. The amount of glucose taken up is determined with the aid of LSC (liquid scintillation counting). However, the amount of a hexose which is taken up by a yeast strain provided as has just been described above can also be determined by growth tests on media with glucose as the only carbon source. To this end, the growth rate of the strain is determined after addition of the compound, for example by regularly measuring the optical density of the culture at 600 nm, and this value is compared with the growth rate of a control strain (for example yeast wild-type strain).

Providing a compound is done in particular by chemical synthesis, or by isolating chemicals from biological organisms. Chemical synthesis may also be automated. The compounds obtained by synthesis or isolation can be dissolved in a suitable solvent. Suitable solvents are, in particular, aqueous solutions comprising a particular amount of an organic solvent such as, for example, DMSO (dimethyl sulfoxide).

Contacting a strain of the yeast with a compound for identifying a compound which increases or reduces the amount of a hexose transported by means of a Glut4 protein is done in particular in automated laboratory systems provided for this purpose. Such systems can be composed of specifically prepared chambers with recesses, of microtiter plates, Eppendorf tubes or laboratory glassware. Automated laboratory systems are generally designed for high throughput rates. A process like what has just been described which is carried out with the aid of an automated laboratory system is therefore also referred to as HTS (high throughput screening).

After contacting the yeast with the compound, the amount of a hexose, in particular glucose, which is transported by the yeast cell into the interior of the cell under these conditions is determined. To this end, the same procedure may be used which has already been described for determining the glucose uptake for a strain which has not been contacted with a compound.

The identification of a compound which increases or reduces the amount of a hexose transported by means of a Glut4 protein is carried out by comparing the amount of the hexose taken up into the strain before and after contacting it with the compound.

The invention furthermore relates to a pharmaceutical comprising a compound which has been identified and, if appropriate, further developed by the method which has just been described using the Glut4 gene, and to adjuvants for formulating the pharmaceutical for the treatment of diabetes or adiposity. The further development of a compound which has been identified means that, firstly, the specificity with regard to the target protein, in this case Glut4, is improved, secondly that the availability in the animal or human organism is increased and thirdly that any existing undesired side effects are reduced. To this end, a series of methods is available to the skilled worker, including, for example but not by way of limitation, the use of pharmacological animal models such as diabetic rats or ob/ob mice, the use of biochemical in-vitro measurements, the use of virtual structure models of compounds and of the Glut4 protein. Adjuvants for the formulation of a pharmaceutical make possible the conditioning of the active substance with the purpose of tailoring the application, distribution and development of action of the active ingredient to the application in question. Examples of such adjuvants are fillers, binders, disintegrants or glidants such as lactose, sucrose, mannitol, sorbitol, cellulose, starch, dicalcium phosphate, polyglycols, alginates, polyvinylpyrrolidone, carboxymethylcellulose, talc or silicon dioxide.

Diabetes is evidenced by the excretion of glucose together with the urine combined with an abnormal increase in the blood glucose level (hyperglycemia) owing to a chronic metabolic condition due to lack of insulin or a reduced insulin effect. The lack of, or reduced, insulin effect leads to incomplete absorption and conversion of the glucose taken up into the blood by the body cells. In fatty tissue, insulin-antagonistic hormones have the effect of increasing lipolysis, which entails an increase in the free fatty acid levels in the blood.

Adiposity (obesity) is the abnormal weight gain owing to an energy imbalance due to excessive intake of calories, which constitutes a health hazard.

The invention furthermore relates to the use of a compound which has been identified, and, if appropriate, further developed by a method using the Glut4 protein for the preparation of a pharmaceutical for the treatment of diabetes or adiposity. Pharmaceuticals are dosage forms of pharmacologically active substances for the therapy of diseases or bodily malfunctions in humans and animals. For example, powders, granules, tablets, pills, lozenges, sugar-coated tablets, capsules, liquid extracts, tinctures and syrups are known for oral therapy. Examples which are used for external administration are aerosols, sprays, gels, ointments or powders. Injectable or infusible solutions allow parenteral administration, with vials, bottles or prefilled syringes being used. These and other pharmaceuticals are known to the skilled worker in the field of pharmaceutical technology.

The invention furthermore relates to a method of identifying a compound which increases or reduces the amount of a hexose transported by means of a Glut1 protein, with the following process steps:

a) Providing a strain of the yeast *Saccharomyces cerevisiae* which can no longer grow on substrates with hexoses as the only carbon source and whose ability of growing on a substrate with a hexose as the only carbon source is restored when it expresses a GLUT1 gene, this strain comprising a GLUT1 gene under the functional control of a promoter which can be expressed in yeast;

b) Determining the amount of a hexose which is taken up into this strain provided in accordance with a);

c) Providing a compound;

d) Contacting a strain of the yeast provided in accordance with a) with a compound provided in accordance with c);

e) Determining the amount of a hexose which is taken up into the yeast strain after contacting in accordance with d);

f) Identifying a compound which increases or reduces the amount of a hexose transported by means of a Glut1 protein by comparing the amount of the hexose taken up into the strain before and after contacting in accordance with d), which is determined in accordance with b) and e).

To provide a yeast according to the invention, a strain of a yeast *Saccharomyces cerevisiae* which no longer forms hexose transporters owing to deletion of the genomic sequences and, as a consequence, is no longer capable of growing on substrates with hexoses as the only carbon source, but whose ability of growing on a substrate with a hexose as the only carbon source is restored when it expresses a GLUT1 gene, is isolated in a first step. Such strains are deposited at the Deutsche Sammlung von Mikroorganismen und Zellkulturen GmbH under the numbers DSM 14031, DSM 14032 or DSM 14034.

In the yeast *Saccharomyces cerevisiae*, 17 hexose transporters and additionally three maltose transporters are known, which are capable of transporting hexoses into the yeast. A strain is known in which all of the transporters which are capable of taking up hexoses have been removed by deletion. The generation and characterization of this yeast strain is described in Wieczorke et al., FEBS Lett. 464, 123–128 (1999). This strain is not capable of growing on a substrate with a hexose as the only carbon source. If a plasmid vector which carries a Glut1 gene under the control of a yeast promoter is transformed into such a yeast strain, no glucose transport takes place nevertheless. The functional expression of Glut1 requires further adaptations of this yeast strain in order to make possible the transport of glucose by means of Glut1. Such yeast strains which take up glucose into the cells by means of a single glucose transporter Glut1 can be isolated on substrates with glucose as the only carbon source. To this end, a yeast strain which no longer expresses intact hexose-transporting proteins is transformed with a yeast vector which carries a GLUT1 gene under the functional control of a yeast promoter. These yeast cells which have been transformed in this manner are plated onto a medium comprising glucose as the only carbon source and are incubated thereon. After a few days incubation at, for example, 30° C., the growth of individual colonies is observed. One of these colonies is isolated. If the yeast plasmid is removed from this colony, no growth takes place on the medium with glucose as the only carbon source. If a yeast vector carrying a GLUT1 gene under the functional control of a yeast promoter is now transformed into this strain, which no longer comprises vector plasmid, then this strain regains the ability of growing on a medium with glucose as the only carbon source.

To transform a yeast strain, a GLUT1 gene from humans, mice or rats is used in particular. Polynucleotide sequences and amino acid sequences for Glut1 are disclosed under the following code numbers of the databases indicated: EMBL: M20653 (cDNA; human), EMBL:M13979 (cDNA; rat), EMBL:M23384 (cDNA; mouse), Swissprot:P11166 (protein; human), Swissprot:P11167 (protein; rat), Swissprot: P17809 (protein; mouse).

The generation of such a yeast strain is described in the examples. Providing the yeast furthermore requires growing this yeast. Growing takes place by standard methods of microbiology in suitable media. Suitable media for growing a yeast are, for example, complete media, in particular YPD medium (yeast extract/peptone/dextrose medium) or selective media. The yeast cells are grown in these media, separated from the medium by centrifugation after growing, and, for the purposes of the method, suspended in an aqueous medium comprising, inter alia, buffer substances, salts or other additives, to give an aqueous suspension. The skilled worker will find information on growing yeasts in "Methods in Yeast Genetics, 1997: A Cold Spring Harbor Laboratory Course Manual; Adams Alison (Edt.); Cold Spring Harbor Laboratory; ISBN: 0-87969-508-0", which has already been mentioned above.

In a preferred embodiment of this method, a strain of the yeast *Saccharomyces cerevisiae* is provided which comprises a GLUT1 gene under the functional control of a promoter which can be expressed in yeast. Such strains which are suitable for this method were deposited at the Sammlung fur Mikroorganismen und Zellkulturen GmbH under the number DSM 14033, DSM 14026 or DSM 14033.

A GLUT1 gene as constituent of a plasmid is disclosed in SEQ ID No. 11 or SEQ ID No. 12. SEQ ID No. 11 comprises the sequence of the yeast vector Yep4H7-HsGlut1. This plasmid comprises the polynucleotide sequence of a human GLUT1 gene under the functional control of an HXT7 promoter. SEQ ID No. 12 comprises the polynucleotide sequence of the yeast vector H2rg1g2. This plasmid comprises the polynucleotide sequence of a GLUT1 gene from rats under the functional control of the HXT2 promoter.

The amount of a hexose which is taken up by a yeast strain provided as has just been described above can be determined by uptake studies with radiolabeled glucose. To this end, a specific amount of yeast cells, for example an amount with a wet weight of 60 mg, is suspended in, for example, 100 μl of a buffer and treated with a defined amount of $^{14}$C- or $^3$H-labeled glucose as the only carbon source. The cells are incubated, and defined amounts of the cells are sampled at specific times. The amount of glucose taken up is determined with the aid of LSC (liquid scintillation counting).

Providing a compound is done in particular by chemical synthesis, or by isolating chemicals from biological organisms. Chemical synthesis may also be automated. The compounds obtained by synthesis or isolation can be dissolved in a suitable solvent. Suitable solvents are, in particular, aqueous solutions comprising a particular amount of an organic solvent such as, for example, DMSO (dimethyl sulfoxide).

Contacting a strain of the yeast with a compound for identifying a compound which increases or reduces the amount of a hexose transported by means of a Glut1 protein is done in particular in automated laboratory systems provided for this purpose. Such systems can be composed of specifically prepared chambers with recesses, of microtiter plates, of Eppendorf tubes or of laboratory glassware. Automated laboratory systems are generally designed for high throughput rates. A process like what has just been described which is carried out with the aid of an automated laboratory system is therefore also referred to as HTS (high throughput screening).

After contacting the yeast with the compound, the amount of a hexose, in particular glucose, which is transported by the yeast cell into the interior of the cell under these conditions is determined. To this end, the same procedure may be used which has already been described for determining the glucose uptake for a strain which has not been contacted with a compound.

The identification of a compound which increases or reduces the amount of a hexose transported by means of a Glut1 protein is carried out by comparing the amount of the hexose taken up into the strain before and after contacting it with the compound.

The invention furthermore relates to a pharmaceutical comprising a compound which has been identified and, if appropriate, further developed by the process which has just been described using the Glut1 gene, and to adjuvants for formulating the pharmaceutical for the treatment of diabetes or adiposity. The further development of a compound which has been identified means that, firstly, the specificity with regard to the target protein, in this case Glut4, is improved, secondly that the availability in the animal or human organism is increased and thirdly that any existing undesired side effects are reduced. To this end, a series of methods is available to the skilled worker, including, for example but not by way of limitation, the use of pharmacological animal models such as diabetic rats or ob/ob mice, the use of biochemical in-vitro measurements, the use of virtual structure models of compounds and of the Glut1 protein. Adjuvants for the formulation of a pharmaceutical make possible the conditioning of the active substance with the purpose of tailoring the application, distribution and development of action of the active ingredient to the application in question. Examples of such adjuvants are fillers, binders, disintegrants or glidants such as lactose, sucrose, mannitol, sorbitol, cellulose, starch, dicalcium phosphate, polyglycols, alginates, polyvinylpyrrolidone, carboxymethylcellulose, talc or silicon dioxide.

Diabetes is evidenced by the excretion of glucose together with the urine combined with an abnormal increase in the blood glucose level (hyperglycemia) owing to a chronic metabolic condition due to lack of insulin or a reduced insulin effect. The lack of, or reduced, insulin effect leads to incomplete absorption and conversion of the glucose taken up into the blood by the body cells. In fatty tissue, insulin-antagonistic hormones have the effect of increasing lipolysis, which entails an increase in the free fatty acid levels in the blood. Adiposity (obesity) is the abnormal weight gain owing to an energy imbalance due to excessive intake of calories, which constitutes a health hazard.

The invention furthermore relates to the use of a compound which has been identified and, if appropriate, further developed by a method using the Glut1 protein for the preparation of a pharmaceutical for the treatment of diabetes or adiposity. Pharmaceuticals are dosage forms of pharmacologically active substances for the therapy of diseases or bodily malfunctions in humans and animals. For example, powders, granules, tablets, pills, lozenges, sugar-coated tablets, capsules, liquid extracts, tinctures and syrups are known for oral therapy. Examples which are used for external administration are aerosols, sprays, gels, ointments or powders. Injectable or infusible solutions allow parenteral administration, with vials, bottles or prefilled syringes being used. These and other pharmaceuticals are known to the skilled worker in the field of pharmaceutical technology.

The invention furthermore relates to the polynucleotide sequence of SEQ ID No. 13 and to the polynucleotide sequence of SEQ ID No. 14. The polynucleotide sequences of SEQ ID No. 13 and 14 encode mutations of the rat Glut1 gene which lead to the substitution of individual amino acids in the protein in question. The polynucleotide sequence of SEQ ID No. 13 encodes a Glut1 protein with a substitution of valine with methionine in position 69 of the amino acid chain. The polynucleotide sequence of SEQ ID No. 14 encodes a Glut1 protein where an alanine is substituted with methionine in position 70 of the amino acid chain. Both protein mutants support the uptake of glucose even in a strain whose hexose transporters have been switched off by deletion, but which does not yet support the uptake of glucose by the wild-type Glut1 protein. Such mutants can be obtained for example via selection for suppressor mutations or via in-vitro mutagenesis.

The invention furthermore relates to a Glut1 protein which is encoded by the polynucleotide sequence of SEQ ID No. 13 or 14.

The invention also relates to yeast strains comprising a polynucleotide sequence of SEQ ID No. 13 or a polynucleotide sequence of SEQ ID No. 14. Such yeast strains are deposited at the Deutsche Sammlung für Mikroorganismen und Zellkulturen GmbH as DSM 14026 and DSM 14027. To generate these strains, yeast vectors corresponding to SEQ ID No. 13 or 14 are transformed into a yeast strain which is no longer capable of growth on substrates with hexoses as the only carbon source and whose ability of growing on a substrate with hexose as the only carbon source is eventually restored when a Glut1 gene is expressed in this strain. Then, after transformation, the cells are plated onto a medium with glucose as the only carbon source. The colonies growing on this medium are isolated. The yeast strain which has been transformed in this manner is suitable for example for carrying out a method of identifying a compound which increases or reduces the amount of a hexose transported by means of a Glut1 protein.

Abbreviations

HXT hexose transporter

ORF open reading frame

PCR polymerase chain reaction

EXAMPLES

Growing the Yeast Strains

All of the yeast strains described herein were derived from strain CEN.PK2-1C (MATa leu2-3, 112 ura3-52 trp1-289 his3-Δ1 MAL2-8$^c$ SUC2). The generation of a yeast strain with deletions in the hexose transporter genes (HXT) was described by Wieczorke et al., FEBS Lett. 464, 123–128 (1999): EBY.18ga (MATa Δhxt1-17 Δgal2 Δagt1 Δstl1 leu2-3, 112 ura3-52trp1-289 his 3-Δ1 MAL2-8$^c$ SUC2), EBY.VW4000 (MATa Δhxt1-17 Δgal2 Δagt1 Δmph2 Δmph3 Δstl1 leu2-3, 112 ura3-52 trp1-289 his3-Δ1 MAL2-8$^c$ SUC2). The media were based on 1% yeast extract and 2% peptone (YP), while the minimal media were composed of 0.67% Difco yeast nitrogen base without amino acids (YNB) and comprised additives for auxotrophism requirements and different carbon sources. The yeast cells were grown aerobically at 30° C. on an orbital shaker or on Agar plates. Cell growth was monitored by measuring the optical density at 600 nm ($OD_{600}$).

Glucose Uptake Determination

The glucose transport was measured as the uptake of D-[U-$^{14}$C]-glucose (Amersham), and the kinetics parameters were determined from Eadie-Hofstee graphs. The cells were spun, washed with phosphate buffer and resuspended in phosphate buffer at a concentration of 60 mg (fresh weight) per ml. Glucose uptake was determined at glucose concentrations of between 0.2 and 100 mM, and the specific activity of the substrate ranged between 0.1 and 55.5 kBq $\mu mol^{-1}$. Cells and glucose solutions were preincubated for 5 minutes at 30° C. Glucose uptake was started by treating the cells with radioactive glucose. After incubation for 5 seconds, 10 ml of ice-cold stop buffer (0.1 M $KiPO_4$, pH 6.5, 500 mM glucose) were added, and the cells were filtered rapidly on glass fiber filters (Ø=24 mm, Whatman). The filters were washed rapidly three times with ice-cold buffer, and the radioactivity incorporated was measured in a liquid scintillation counter. Inhibition by cytochalasin B (final concentration 20 μM, dissolved in ethanol) was measured in a 15-second-uptake test with 50 mM or 100 mM radioactive glucose after incubating the cells for 15 minutes in the presence of the inhibitor or only of the solvent.

Construction of H2rg4g2 (SEQ ID No. 10) and H2rg1g2 (SEQ ID No. 12)

H2rg4g2 and H2rg1g2 are DNA constructs comprising an HXT2 promoter (promoter of the yeast glucose transport protein 2) linked functionally to a GLUT4 gene (in SEQ ID No. 10) or GLUT1 gene (in SEQ ID No. 12) from rats. An 0.5 kb SalI/EcoRI-GAL2 promoter fragment of plasmids GLUT1-pTV3 and GLUT4-pTV3 (Kasahara and Kasahara, Biochem J. 315, 177–182 (1996); Kasahara and Kasahara, Biochim. Biophys. Acta 857, 146–154 (1997)) was substituted in each case for an 0.5 kb DNA fragment comprising the yeast HXT2 promoter from −452 bp through +9 bp (Genbank: P23585).

Construction of YEp4H7-HsGLUT1 (SEQ ID No. 11) and YEp4H7-HsGLUT4 (SEQ ID No. 9)

YEp4H7-HsGLUT1 and YEp4H7-HsGLUT4 are plasmids in which a promoter fragment of positions −392 through −1 of the HXT7 promoter (promoter of the HXT7 gene) is linked functionally to a human GLUT1 gene (in SEQ ID No. 11) or GLUT4 gene (in SEQ ID No. 9). The fragment of the promoter was used since the complete HXT7 promoter is repressed by glucose.

A 0.4 kb SacI/SpeI-MET25 promoter fragment from p426MET25 (Mumberg et al., Nucleic Acids Res. 22, 5767–5768 (1994)) was substituted with an 0.4 kb DNA fragment comprising an HXT7 promoter fragment from positions −392 through −1, which had been amplified by means of PCR from an HXT7 gene (Genbank:P39004) as template, using the primers P426H7-1 (SEQ ID No. 1) and P426H7-2 (SEQ ID No. 2), giving rise to plasmid YEp4H7 (SEQ ID No. 15). The human GLUT1 and GLUT4 ORFs (open reading frames) were amplified over 10 cycles by means of PCR with the primer pairs HSG1-F7/T2-HSG1 (SEQ ID No. 3.4) for Glut1 and HSG4-F7/T2-HSG4 (SEQ ID No. 5.6) for Glut4 and a human GLUT1 (EMBL: M20653) and human GLUT4 cDNA (Genbank:M20747) as templates. The PCR products were reamplified over 10 cycles using the primers T71-ORF (SEQ ID No. 7) and T2-HSG1 (SEQ ID No. 4) or T2-HSG4 (SEQ ID No. 6). Upstream and downstream of the GLUT ORF sequences, the PCR end products contain sequences which are homologous to the HXT7 promoter region or the CYC1 termination region (iso-cytochrome c1) of plasmid YEp4H7. They were transformed into the yeast strain EBY.F4-1 together with the EcoRI-linearized YEp4H7, whereupon, following homologous recombination in yeast, the transformation products were selected for uracil prototrophism in a 2% strength maltose medium.

Expression of GLUT1 and GLUT4 from Rats in a Hexose-transport-deficient Yeast Strain The yeast multicopy expression plasmids GLUT1-pTV3e and GLUT4-pTV3e carry the glucose transporter genes GLUT1 and GLUT4 from rats under the control of the galactose-inducible and glucose-repressible yeast GAL2 promoter. In the two constructs, the GAL2 promoter was replaced by the glucose-inducible yeast HXT2 promoter. These vectors were transformed into the yeast strain EBY.18ga (Δhxt), which is not capable of taking up any hexoses whatsoever and can therefore not grow on media with glucose or other hexoses as the only carbon source. The cells were plated onto a tryptophan-free synthetic medium with maltose as carbon source. The transformants were plated onto the same basal medium without maltose, but with different glucose concentrations (5 mM, 10 mM, 50 mM, 100 mM), using the replica-plating method. The transformants did not grow on the different glucose media, not even when incubated for up to one week at 30° C. This proves that the Glut1 and Glut4 glucose transporters do not support glucose uptake in a normal *S. cerevisiae* strain.

Glucose Uptake via the Glut1 Transporter in Yeast Cells

It emerged that, following prolonged incubation of Glut1 transformants of strain EBY.18ga on a glucose medium, colonies (termed suppressor mutants or suppressor colonies hereinbelow) grew, and these were obviously capable of taking up, and converting, glucose. The GLUT1 and GLUT4 transformants were therefore plated onto agar plates with a YNB medium with 10 mM of glucose as the only carbon source. Following irradiation with UV light at a sublethal dose, the cells were incubated for 7–14 days at 30° C. While no suppressor colonies were observed in the case of the GLUT4 transformants, several suppressor colonies which were capable of growing on glucose grew on the agar plates with the GLUT1 transformants. Several of the GLUT1 suppressor mutants were grown over 15 generations in nonselective YP maltose medium. All cells which had lost their plasmids were no longer capable of growing on media with glucose as the carbon source. It was thus possible to demonstrate that growth on glucose as the only carbon source was GLUT1-dependent. After the retransformation of the original wild-type H2rg1g2 plasmid into these cells, one of several yeast strains regains the ability of growing on glucose. This confirms that this strain comprises, in its genome, a mutation which eliminates the inhibitory action on functional GLUT1 expression. The mutated allele was termed fgy1-1 (which stands for "functional expression of GLUT1 in yeast"), and the strain was termed EBY.S7.

H2rg1g2 plasmids were isolated from other suppressor mutants, amplified in *E. coli* and transformed back into the original glucose-transport-deficient yeast strain EBY.18ga (Δhxt). Several of these plasmids allowed growth on a synthetic medium with 10 mM glucose as the only carbon source. Accordingly, these GLUT1 sequences comprised mutations which converted the corresponding GLUT1 protein in the yeast into a functional glucose transporter. For example, such mutants comprised a substitution of valine with methionine at the position of amino acid 69 (SEQ ID No.13) or a substitution of alanine with methionine at the position of amino acid 70 (SEQ ID No. 14). The mutant of SEQ ID No. 13 was found during screening of the mutants as described above. The mutant of SEQ ID No. 14 was obtained by in-vitro mutagenesis as shown hereinbelow. The principle of the in-vitro mutagenesis method applied is described by Boles and Miosga (1995) (Boles and Miosga, Curr Genet. 28, 197–198 (1995)). In a first PCR reaction, plasmid YEpH2-rGLUT1 (20 ng) as DNA template was employed together with the primers seqhxt2 (SEQ ID No. 16) and glutmet2 (SEQ ID No. 17) (in each case 100 pmol) (PCR conditions: 95° C. 45 sec, 50° C. 30 sec, 72° C. 2 min, 25 cycles, taq polymerase). The primer glutmet2 contains a base sequence which is modified over the normal GLUT1 gene and which leads to a substitution of alanine with methionine at the position of amino acid 70 of GLUT1 from rats. The resulting PCR fragment was purified by agarose gel electrophoresis followed by gel extraction. In a second PCR reaction, the purified PCR fragment (20 ng) was used together with plasmid GLUT1-pTV3 (Kasahara and Kasahara, Biochem J. 315, 177–182 (1996)) as DNA template (50 ng) and together with the primers seqhxt2 and seq2gal2 (SEQ ID No. 18) (in each case 100 pmol) (PCR conditions: 95° C. 45 sec, 54° C. 30 sec, 72° C. 2 min, 20 cycles, taq polymerase). Since the primer seqhxt2 only binds to the fragment of the first PCR reaction, only those DNA sequences were amplified in this second PCR reaction which lead to a substitution of alanine with methionine at the position of amino acid 70. The resulting PCR fragment with the mutated GLUT1 gene was purified by means of agarose gel electrophoresis followed by gel extraction, and exchanged for the wild-type GLUT1 gene in plasmid YEpH2-rGLUT1. This plasmid (SEQ ID No. 14) was transformed into the glucose-transport-deficient yeast strain EBY.18ga (Δhxt) and allowed growth on a synthetic medium with glucose as the only carbon source.

Strains of the Yeast *Saccharomyces cerevisiae*, which Take Up Glucose via the Glut4 Transporter Strain EBY.S7 (Δhxt fgy1-1) apparently comprises a genome mutation, viz. fgy1-1, which allows Glut1 to become functional in yeast and to support the uptake of glucose across the plasma membrane into the cells.

Following transformation of strain EBY.S7 (Δhxt fgy1-1) with H2rg4g2, suppressor colonies were isolated which were capable of growth on media with glucose as the only carbon source.

Nine of these GLUT4 suppressor mutants were grown for over 15 generations in nonselective YP maltose medium. All cells which had lost their plasmids were likewise no longer capable of growing on 10 mM glucose media, which confirms that the earlier growth was GLUT4-dependent. The H2rg4g2 plasmids were reisolated from the nine suppressor strains, amplified in *E. coli* and transformed back into the original glucose-transport-deficient yeast strain EBY.S7. None of the plasmids allowed growth on a synthetic medium with 10 mM glucose as the only carbon source. This demonstrated that they comprised no "activated" mutant forms of GLUT4. Following retransformation of the original wild-type H2rg4g2 plasmid into the nine, now plasmid-free, suppressor strains, all of these strains regained the ability of growing on glucose, as opposed to transformants which comprised a control vector without Glut4 transport protein gene. The corresponding mutations of this strain were termed fgy4-X (x=1–9). The mutated alleles fgy4-X caused functional GLUT4 expression of a GLUT4 gene expressed in these strains. The object of the invention was herewith achieved.

An overview of the yeast strains according to the invention which have been used is found in the table.

The table gives an overview of the yeast strains used in the present invention including the genotype, the growth conditions required for growing them, and the respective deposit number at the Deutsche Sammlung von Mikroorganismen und Zellkulturen GmbH.

TABLE

List of strains

| No. | Strain | Genotype | Phenotype | Plasmid | DSM-No. |
|---|---|---|---|---|---|
| 1 | EBY.18ga | M4TaΔhxt1-17Δgal2Δagt1 Δst1 leu2-3, 112 ura3-52 trp1-289 his3-Δ1 MAL2-8$^C$ SUC2 | Grows with 1% maltose as C-source; auxotrophic for glucose, leucine, tryptophan, histidine and uracil | — | DSM 14031 |
| 2 | EBY.18ga | M4TaΔhxt1-17Δgal2Δagt1 Δst1 leu2-3, 112 ura3-52 trp1-289 his3-Δ1 MAL2-8$^C$ SUC2 | Grows with 0.2% glucose or 1% maltose as C source; auxotrophic for leucine, histidine and uracil | YEpH2-rGLUT1V69M (selection marker TRP1) | DSM 14026 |
| 3 | EBY.18ga | MATaΔhxt1-17 Δgal2 Δagt1 Δstl1 leu2-3, 112 ura3-52 trp1-289 his3-Δ1 MAL2-8$^C$ SUC2 | Grows with 0.2% glucose or 1% maltose as C source; auxotrophic for leucine, histidine and uracil | YEpH2-rGLUT1A70M (selection marker TRPI) | DSM 14027 |
| 4 | EBY.S7 | MATaΔhxt1-17 Δgal2 Δagt1 Δstl1 fgyl-1 leu2-3, 112 ura3-52 trp1-28, 9 his3-Δ1 MAL2-8$^C$ SUC2 | Grows with 1% maltose as C-source; auxotrophic for glucose, leucine, tryptophan, histidine and uracil | — | DSM 14032 |
| 5 | EBY.S7 | MATaΔhxt1-17 Δgal2 Δagt1 Δstl1 fgyl-1 leu2-3, 112 ura3-52 trp1-28, 9 his3-Δ1 MAL2-8$^C$ SUC2 | Grows with 0.2% glucose or 1% maltose as C source; auxotrophic for leucine, tryptophan and histidine | YEp4H7-HsGLUT1 (selection marker URA3) | DSM 14033 |
| 6 | EBY.VW4000 | MATaΔhxt1-17 Δgal2 Δagt1 Δstl1 Δmph2 Δmph3 leu2-3, 112 ura3-52 trp1-289 his3-Δ1 MAL2-8$^C$ SUC2 | Grows with 1% maltose as C-source; auxotrophic for glucose, leucine, tryptophan, histidine and uracil | — | DSM 14034 |
| 7 | EBY.f4-1 | MATa Δhxt1-17 Δgal2 Δagt1 Δstl1 fgy4-1 fgy4-1 leu2-3, 112 ura3-52 trp1-289 his3-Δ1 MAL2-8$^C$ SUC2 | Grows with 1% maltose as C-source; auxotrophic for glucose, leucine, tryptophan, histidine and uracil | — | DSM 14035 |
| 8 | EBY.f4-4 | MATa Δhxt1-17 Δgal2 Δagt1 Δstl1 fgy4-4 fgy4-1 leu2-3, 112 ura3-52 trp1-289 his3-Δ1 MAL2-8$^C$ SUC2 | Grows with 1% maltose as C-source; auxotrophic for glucose, leucine, tryptophan, histidine and uracil | — | DSM 14036 |
| 9 | EBY.f4-7 | MATa Δhxt1-17 Δgal2 Δagt1 Δstl1 fgy4-7 fgy4-1 leu2-3, 112 ura3-52 trp1-289 his3-1 MAL2-8$^C$ SUC2 | Grows with 1% maltose as C-source; auxotrophic for glucose, leucine, tryptophan, histidine and uracil | — | DSM 14037 |
| 10 | EBY.f4-1 | MATaΔhxt1-17 Δgal2 Δagt1 Δstl1 fgy4-1 fgy4-1 leu2-3, 112 ura3-52 trp1-289 his3-Δ1 MAL2-8$^C$ SUC2 | Grows with 0.2% glucose or 1% maltose as C source; auxotrophic for leucine, tryptophan and histidine | YEp4H7-HsGLUT4 (selection marker URA3) | DSM 14038 |
| 11 | EBY.f4-4 | M4Ta Δhxt1-17 Δgal2 Δagt1 Δstl1 fgy4-4 fgy4-1 leu2-3, 112 ura3-52 trp1-289 his3-Δ1 MAL2-8$^C$ SUC2 | Grows with 0.2% glucose or 1% maltose as C source; auxotrophic for leucine, tryptophan and histidine | YEp4H7-HsGLUT4 (selection marker URA3) | DSM 14039 |
| 12 | EBY-f4-7 | MATa Δhxt1-17 Δgal2 Δagt1 Δstl1 fgy4-7 fgy4-1 leu2-3, 112 ura3-52 trp1-289 his3-Δ1 MAL2-8$^C$ SUC2 | Grows with 0.2% glucose or 1% maltose as C source; auxotrophic for leucine, tryptophan and histidine | YEp4H7-HsGLUT4 (selection marker URA3) | DSM 14040 |

Basal medium: 0.67% yeast nitrogen base without amino acids (Difco); pH 6.2. Supplementation of the auxotrophisms: leucine (0.44 mM), tryptophan (0.19 mM), uracil (0.44 mM). Maltose can be employed at a concentration of between 1 and 2%; glucose between 0.2 and 2% (better growth at lower concentrations). All strains listed in this table were deposited at the Deutsche Sammlung von Mikroorganismen aund Zellkulturen GmbH at Mascheroder Weg 1b, D38124 Braunschweig, Germany, on January 23, 2001.

We claim:

1. A strain of the yeast *Saccharomyces cerevisiae* which can no longer grow on substrates with hexoses as the only carbon source and whose ability of growing on a substrate with a hexose as the only carbon source is restored when a GLUT4 gene is expressed in this strain, wherein said strain is deposited at the Deutsche Sammlung von Mikroorganismen und Zellkulturen GmbH as DSM 14035, DSM 14036 or DSM 14037.

2. The strain of the yeast *Saccharomyces cerevisiae* which comprises a GLUT4 gene and is deposited at the Deutsche Sammlung von Mikroorganismen und Zellkulturen GmbH as DSM 14038, DSM 14039 or DSM 14040.

3. A method for generating a strain of the yeast *Saccharomyces cerevisiae*, comprising the steps of:
   a) providing a strain of *Saccharomyces cerevisiae* yeast,
   b) eliminating the function of all hexose transporters of the strain of yeast from a) by mutating or deleting the relevant genomic sequences.
   c) subjecting the strain from step b) to further mutagenesis, and
   d) screening the mutated strains from step c) for the ability to grow on a substrate with a hexose as the only carbon source when a GLUT4 gene is expressed in the strain.

4. The method of claim 3, wherein step c) comprises:
   $c_1$) transforming the strain from step b) with a vector comprising the GLUT1 gene under the functional control of a promoter which can be expressed in yeast,
   $c_2$) subjecting the transformed strain of step $c_1$) to further mutagenesis,
   $c_3$) screening the transformed, mutated strain from step $c_2$) for the ability to grow on a substrate with a hexose as the only carbon source,
   $c_4$) isolating a transformed, mutated strain identified in step $c_3$) as having the ability to grown on a substrate with a hexose as the only carbon source, and
   $c_5$) removing the vector comprising the GLUT1 gene from the isolated strain of step $c_4$).

* * * * *

SEQUENCE LISTING

<160> NUMBER OF SEQ ID NOS: 18

<210> SEQ ID NO 1
<211> LENGTH: 25
<212> TYPE: DNA
<213> ORGANISM: Homo sapiens

<400> SEQUENCE: 1
ctagagctcg taggaacaat ttcgg                                    25

<210> SEQ ID NO 2
<211> LENGTH: 60
<212> TYPE: DNA
<213> ORGANISM: Homo sapiens

<400> SEQUENCE: 2
cgactagtgt gatggtgatg gtgatgcatg ttaactttt gattaaaatt aaaaaaactt    60

```
<210> SEQ ID NO 3
<211> LENGTH: 35
<212> TYPE: DNA
<213> ORGANISM: Homo sapiens

<400> SEQUENCE: 3
ttaattttaa tcaaaaaatg gagcccagca gcaag                          35

<210> SEQ ID NO 4
<211> LENGTH: 52
<212> TYPE: DNA
<213> ORGANISM: Homo sapiens

<400> SEQUENCE: 4
acatgactcg aggtcgacgg tatcgataag cttatcacac ttgggaatca gc       52

<210> SEQ ID NO 5
<211> LENGTH: 35
<212> TYPE: DNA
<213> ORGANISM: Homo sapiens

<400> SEQUENCE: 5
ttaattttaa tcaaaaaatg ccgtcgggct tccaa                          35

<210> SEQ ID NO 6
<211> LENGTH: 52
<212> TYPE: DNA
<213> ORGANISM: Homo sapiens

<400> SEQUENCE: 6
acatgactcg aggtcgacgg tatcgataag cttatcagtc gttctcatct gg       52

<210> SEQ ID NO 7
<211> LENGTH: 73
<212> TYPE: DNA
<213> ORGANISM: Rattus norvegicus

<400> SEQUENCE: 7
caaagaataa acacaaaaac aaaaagttttt tttaattttta atcaaaaaat gtctgaattc    60
agcagcaaga agg                                                         73

<210> SEQ ID NO 8
<211> LENGTH: 71
<212> TYPE: DNA
<213> ORGANISM: Rattus norvegicus

<400> SEQUENCE: 8 aagtttctttt gtctccgtcc cactcaactt tctgagaaca aatgatcgac aaataatagg     60
tttaggtaag g                                                           71

<210> SEQ ID NO 9
<211> LENGTH: 7828
<212> TYPE: DNA
<213> ORGANISM: Homo sapiens

<400> SEQUENCE: 9
atgccgtcgg gcttccaaca gataggctcc gaagatgggg aaccccctca gcagcgagtg     60
actgggaccc tggtccttgc tgtgttctct gcggtgcttg ctccctgca gtttgggtac     120 aacattgggg tcatcaatgc ccctcagaag gtgattgaac agagctacaa tgagacgtgg    180
ctggggaggc aggggcctga gggacccagc tccatccctc aggcaccct caccaccctc    240
```

```
tgggccctct ccgtggccat cttttccgtg ggcggcatga tttcctcctt cctcattggt      300
atcatctctc agtggcttgg aaggaaaagg gccatgctgg tcaacaatgt cctggcggtg      360 ctgggggggca gcctcatggg cctggccaac gctgctgcct cctatgaaat gctcatcctt     420
ggacgattcc tcattggcgc ctactcaggg ctgacatcag ggctggtgcc catgtacgtg      480
ggggagattg ctcccactca cctgcggggc ccctgggga cgctcaacca actggccatt       540
gttatcggca ttctgatcgc ccaggtgctg ggcttggagt ccctcctggg cactgccagc     600
ctgtggccac tgctcctggg cctcacagtg ctacctgccc cctgcagct ggtcctgctg       660 cccttctgtc ccgagagccc ccgctacctc tacatcatcc agaatctcga ggggcctgcc     720
agaaagagtc tgaagcgcct gacaggctgg gccgatgttt ctggagtgct ggctgagctg     780
aaggatgaga gcggaagct ggagcgtgag cggccactgt ccctgctcca gctcctgggc       840
agccgtaccc accggcagcc cctgatcatt gcggtcgtgc tgcagctgag ccagcagctc     900
tctggcatca atgctgtttt ctattattcg accagcatct tcgagacagc aggggtaggc     960
cagcctgcct atgccaccat aggagctggt gtggtcaaca cagtcttcac cttggtctcg   1020
gtgttgttgg tggagcgggc ggggcgccgg acgctccatc tcctgggcct ggcgggcatg    1080
tgtggctgtg ccatcctgat gactgtggct ctgctcctgc tggagcgagt tccagccatg   1140
agctacgtct ccattgtggc catctttggc ttcgtggcat tttttgagat tggccctggc   1200
cccattcctt ggttcatcgt ggccgagctc ttcagccagg accccgccc ggcagccatg     1260 gctgtggctg gtttctccaa ctggacgagc aacttcatca ttggcatggg tttccagtat   1320
gttgcggagg ctatgggggcc ctacgtcttc cttctatttg cggtcctcct gctgggcttc    1380
ttcatcttca ccttcttaag agtacctgaa actcgaggcc ggacgtttga ccagatctca   1440
gctgccttcc accggacacc ctctctttta gagcaggagg tgaaacccag cacagaactt    1500
gagtatttag ggccagatga gaacgactga taagcttatc gataccgtcg acctcgagtc    1560
atgtaattag ttatgtcacg cttacattca cgccctcccc ccacatccgc tctaaccgaa   1620
aaggaaggag ttagacaacc tgaagtctag gtccctattt atttttttat agttatgtta   1680
gtattaagaa cgttatttat atttcaaatt tttctttttt ttctgtacag acgcgtgtac    1740
gcatgtaaca ttatactgaa aaccttgctt gagaaggttt tgggacgctc gaaggctta    1800 atttgcggcc ggtacccaat tcgccctata gtgagtcgta ttacgcgcgc tcactggccg   1860
tcgttttaca acgtcgtgac tgggaaaacc ctggcgttac ccaacttaat cgccttgcag   1920
cacatccccc tttcgccagc tggcgtaata gcgaagaggc ccgcaccgat cgcccttccc   1980
aacagttgcg cagcctgaat ggcgaatggg cgacgcgcc ctgtagcggc gcattaagcg    2040
cggcgggtgt ggtggttacg cgcagcgtga ccgctacact tgccagcgcc ctagcgcccg   2100
ctcctttcgc tttcttccct tcctttctcg ccacgttcgc cggctttccc cgtcaagctc   2160
taaatcgggg gctcccttta gggttccgat ttagtgcttt acggcacctc gaccccaaaa   2220
aacttgatta gggtgatggt tcacgtagtg ggccatcgcc ctgatagacg gttttcgcc    2280 ctttgacgtt ggagtccacg ttctttaata gtggactctt gttccaaact ggaacaacac   2340
tcaaccctat ctcggtctat tcttttgatt tataagggat tttgccgatt tcggcctatt    2400
ggttaaaaaa tgagctgatt taacaaaaat ttaacgcgaa ttttaacaaa atattaacgt   2460
ttacaatttc ctgatgcggt attttctcct tacgcatctg tgcggtattt cacaccgcat   2520
agggtaataa ctgatataat taaattgaag ctctaatttg tgagtttagt atacatgcat   2580
ttacttataa tacagttttt tagttttgct ggccgcatct tctcaaatat gcttcccagc   2640
```

```
ctgcttttct gtaacgttca ccctctacct tagcatccct tcccttttgca aatagtcctc    2700 ttccaacaat aataatgtca gatcctgtag agaccacatc atccacggtt ctatactgtt    2760
gacccaatgc gtctcccttg tcatctaaac ccacaccggg tgtcataatc aaccaatcgt    2820
aaccttcatc tcttccaccc atgtctcttt gagcaataaa gccgataaca aaatctttgt    2880
cgctcttcgc aatgtcaaca gtaccettag tatattctcc agtagatagg gagcccttgc    2940
atgacaattc tgctaacatc aaaaggcctc taggttcctt tgttacttct tctgccgcct    3000
gcttcaaacc gctaacaata cctgggccca ccacaccgtg tgcattcgta atgtctgccc    3060
attctgctat tctgtataca cccgcagagt actgcaattt gactgtatta ccaatgtcag    3120
caaattttct gtcttcgaag agtaaaaaat tgtacttggc ggataatgcc tttagcggct    3180
taactgtgcc ctccatggaa aaatcagtca agatatccac atgtgttttt agtaaacaaa    3240
ttttgggacc taatgcttca actaactcca gtaattcctt ggtggtacga acatccaatg    3300
aagcacacaa gtttgtttgc ttttcgtgca tgatattaaa tagcttggca gcaacaggac    3360
taggatgagt agcagcacgt tccttatatg tagctttcga catgatttat cttcgttttcc    3420 tgcaggtttt tgttctgtgc agttgggtta agaatactgg gcaatttcat gtttcttcaa    3480
cactacatat gcgtatatat accaatctaa gtctgtgctc cttccttcgt tcttccttct    3540
gttcggagat taccgaatca aaaaatttc aaagaaaccg aaatcaaaaa aagaataaa    3600 aaaaaatga tgaattgaat tgaaaagctg tggtatggtg cactctcagt acaatctgct    3660
ctgatgccgc atagttaagc cagccccgac acccgccaac acccgctgac gcgcctgac    3720 gggcttgtct gctcccggca tccgcttaca gacaagctgt gaccgtctcc gggagctgca    3780
tgtgtcagag gttttcaccg tcatcaccga aacgcgcgag acgaaagggc ctcgtgatac    3840
gcctattttt ataggttaat gtcatgataa taatggtttc ttagtatgat ccaatatcaa    3900
aggaaatgat agcattgaag gatgagacta atccaattga ggagtggcag catatagaac    3960
agctaaaggg tagtgctgaa ggaagcatac gataccccgc atggaatggg ataatatcac    4020
aggaggtact agactacctt tcatcctaca taaatagacg catataagta cgcatttaag    4080
cataaacacg cactatgccg ttcttctcat gtatatatat atacaggcaa cacgcagata    4140
taggtgcgac gtgaacagtg agctgtatgt gcgcagctcg cgttgcattt tcggaagcgc    4200 tcgtttttcgg aaacgctttg aagttcctat tccgaagttc ctattctcta gaaagtatag    4260
gaacttcaga gcgcttttga aaaccaaaag cgctctgaag acgcactttc aaaaaaccaa    4320
aaacgcaccg gactgtaacg agctactaaa atattgcgaa taccgcttcc acaaacattg    4380
ctcaaaagta tctctttgct atatatctct gtgctatatc cctatataac ctacccatcc    4440
acctttcgct ccttgaactt gcatctaaac tcgacctcta cattttttat gtttatctct    4500
agtattactc tttagacaaa aaattgtag taagaactat tcatagagtg aatcgaaaac    4560
aatacgaaaa tgtaaacatt tcctatacgt agtatataga gacaaaatag aagaaaccgt    4620
tcataatttt ctgaccaatg aagaatcatc aacgctatca ctttctgttc acaaagtatg    4680
cgcaatccac atcggtatag aatataatcg gggatgcctt tatcttgaaa aaatgcaccc    4740
gcagcttcgc tagtaatcag taaacgcggg aagtggagtc aggctttttt tatggaagag    4800
aaaatagaca ccaaagtagc cttcttctaa ccttaacgga cctacagtgc aaaaagttat    4860
caagagactg cattatagag cgcacaaagg agaaaaaaag taatctaaga tgctttgtta    4920 gaaaatagc gctctcggga tgcattttttg tagaacaaaa aagaagtata gattctttgt    4980
```

```
tggtaaaata gcgctctcgc gttgcatttc tgttctgtaa aaatgcagct cagattcttt       5040
gtttgaaaaa ttagcgctct cgcgttgcat ttttgtttta caaaaatgaa gcacagattc       5100
ttcgttggta aaatagcgct ttcgcgttgc atttctgttc tgtaaaaatg cagctcagat       5160
tctttgtttg aaaaattagc gctctcgcgt tgcattttgt ttctacaaaa tgaagcacag       5220
atgcttcgtt caggtggcac ttttcgggga aatgtgcgcg aaccccctat tgtttatttt      5280
ttctaaatac attcaaatat gtatccgctc atgagacaat aaccctgata aatgcttcaa      5340
taatattgaa aaaggaagag tatgagtatt caacatttcc gtgtcgccct tattccctt       5400 tttgcggcat tttgccttcc tgttttgct cacccagaaa cgctggtgaa agtaaaagat       5460
gctgaagatc agttgggtgc acgagtgggt tacatcgaac tggatctcaa cagcggtaag      5520
atccttgaga gttttcgccc cgaagaacgt tttccaatga tgagcacttt taaagttctg      5580
ctatgtggcg cggtattatc cgtattgac gccgggcaag agcaactcgg tcgccgcata       5640
cactattctc agaatgactt ggttgagtac tcaccagtca cagaaaagca tcttacggat      5700
ggcatgacag taagagaatt atgcagtgct gccataacca tgagtgataa cactgcggcc      5760
aacttacttc tgacaacgat cggaggaccg aaggagctaa ccgcttttt gcacaacatg       5820 ggggatcatg taactcgcct tgatcgttgg gaaccggagc tgaatgaagc cataccaaac      5880
gacgagcgtg acaccacgat gcctgtagca atggcaacaa cgttgcgcaa actattaact      5940
ggcgaactac ttactctagc ttcccggcaa caattaatag actggatgga ggcggataaa      6000
gttgcaggac cacttctgcg ctcggccctt ccggctggct ggtttattgc tgataaatct      6060
ggagccggtg agcgtgggtc tcgcggtatc attgcagcac tggggccaga tggtaagccc      6120
tcccgtatcg tagttatcta cacgacgggg agtcaggcaa ctatggatga acgaaataga      6180
cagatcgctg agataggtgc ctcactgatt aagcattggt aactgtcaga ccaagtttac      6240
tcatatatac tttagattga tttaaaactt cattttaat ttaaaaggat ctaggtgaag       6300
atcctttttg ataatctcat gaccaaaatc ccttaacgtg agttttcgtt ccactgagcg      6360
tcagaccccg tagaaaagat caaaggatct cttgagatc cttttttct gcgcgtaatc       6420 tgctgcttgc aaacaaaaaa accaccgcta ccagcggtgg tttgtttgcc ggatcaagag      6480
ctaccaactc tttttccgaa ggtaactggc ttcagcagag cgcagatacc aaatactgtc      6540
cttctagtgt agccgtagtt aggccaccac ttcaagaact ctgtagcacc gcctacatac      6600
ctcgctctgc taatcctgtt accagtggct gctgccagtg gcgataagtc gtgtcttacc      6660
gggttggact caagacgata gttaccggat aaggcgcagc ggtcgggctg aacggggggt      6720
tcgtgcacac agcccagctt ggagcgaacg acctacaccg aactgagata cctacagcgt      6780
gagctatgag aaagcgccac gcttcccgaa gggagaaagg cggacaggta tccggtaagc      6840
ggcagggtcg gaacaggaga gcgcacgagg gagcttccag ggggaaacgc ctggtatctt      6900
tatagtcctg tcgggtttcg ccacctctga cttgagcgtc gatttttgtg atgctcgtca      6960
ggggggcgga gcctatggaa aaacgccagc aacgcggcct ttttacggtt cctggccttt      7020
tgctggcctt tgctcacat gttctttcct gcgttatccc ctgattctgt ggataaccgt       7080
attaccgcct ttgagtgagc tgataccgct cgccgcagcc gaacgaccga gcgcagcgag      7140
tcagtgagcg aggaagcgga agagcgccca atacgcaaac cgcctctccc cgcgcgttgg      7200
ccgattcatt aatgcagctg gcacgacagg tttcccgact ggaaagcggg cagtgagcgc      7260
aacgcaatta atgtgagtta cctcactcat taggcaccc aggctttaca ctttatgctt       7320
ccggctccta tgttgtgtgg aattgtgagc ggataacaat ttcacacagg aaacagctat      7380
```

```
gaccatgatt acgccaagcg cgcaattaac cctcactaaa gggaacaaaa gctggagctc      7440
gtaggaacaa tttcgggccc ctgcgtgttc ttctgaggtt catcttttac atttgcttct      7500
gctggataat tttcagaggc aacaaggaaa aattagatgg caaaaagtcg tctttcaagg      7560
aaaaatcccc accatctttc gagatcccct gtaacttatt ggcaactgaa agaatgaaaa      7620
ggaggaaaat acaaaatata ctagaactga aaaaaaaaa gtataaatag agacgatata       7680
tgccaatact tcacaatgtt cgaatctatt cttcatttgc agctattgta aataataaa      7740 acatcaagaa caaacaagct caacttgtct tttctaagaa caaagaataa acacaaaaac      7800 aaaaagttttt tttaattttta atcaaaaa                                       7828

<210> SEQ ID NO 10
<211> LENGTH: 2386
<212> TYPE: DNA
<213> ORGANISM: Rattus norvegicus

<400> SEQUENCE: 10
tcgactctag aggatcccct taagctaatc cttatgaatc cggagaaaag cggggtcttt       60
taactcaata aaattttccg aaatcctttt tcctacgcgt tttcttcggg aactagatag      120
gtggctcttc cacctgtttt tccatcattt tagtttttcg caagccatgc gtgccttttc      180 gttttttgcga tggcgaacga gggctggaaa aattaacggt acgccgccta acgatagtaa      240
taggccacgc aactggcgtg gacgacaaca ataagtcgcc catttttat gtttttcaaaa      300 cctagcaacc cccaccaaac ttgtcatcgt tcccggattc acaaatgata taaaaagcga      360
ttacaattct acattctaac cagatttgag atttcctctt tctcaattcc tcttatatta      420
gattataaga acaacaaatt aaattacaaa agacttata aagcaacata atgtctgaat      480
tccagcagat cggctctgaa gatggggaac cccctcagca gcgagtgact gggacactgg      540
tccttgctgt attctcagct gtgcttggct cccttcagtt tggctataac attggagtca      600
tcaacgcccc acagaaagtg attgaacaga gctacaatgc aacttggctg gtaggcagg       660 gtcctggggg accggactcc atcccacaag gcaccctcac tacccttttgg gctctctccg      720 tggccatctt ctctgtgggt ggcatgattt cctccttttct cattggcatc atttctcaat      780
ggttgggaag gaaagggct atgctggcca acaatgtctt ggctgtgctg ggggcgccc       840 tcatgggcct agccaatgcc gcggcctcct atgagatact cattctcgga cggttcctca      900
ttggcgccta ctcagggcta acatcagggt tggtgcctat gtatgtggga gaaatcgccc      960
ccactcatct tcggggtgcc ttgggaacac tcaaccaatt ggccatcgtc attggcattc     1020
tggttgccca ggtgttgggt ttggagtcta tgctgggcac agctaccctg tggccattgc     1080
ttctggctat cacagtactc cctgctctcc tgcagctgct tctgttgccc ttctgtcctg     1140
agagcccccg atacctctac atcatccgga acctggaggg gcctgcccga aagagtctaa     1200
agcgcctgac aggctgggct gatgtgtctg atgcactggc tgagctgaag gatgagaaac     1260
ggaagttgga aagagagcgt ccactgtcct tgctgcagct cctgggcagc cgcacccacc     1320
ggcagcctct gattattgca gtggtgctgc agctgagcca gcagctctca ggcatcaatg     1380
ctgtttctca ctattcaacc agcatctttg agttagctgg ggtggaacag ccagcctacg     1440
ccaccatagg agctggtgtg gtcaataccg tcttcacgtt ggtctcggtg ctcttagtag     1500
agcgagctgg gcgacggaca ctccatctcc tgggcctggc aggcatgtgt ggctgtgcca     1560
tcttgatgac ggtggctctg ctgctgctgg agcgggttcc atccatgagt tatgtgtcca     1620
```

| | |
|---|---|
| tcgtggccat atttggcttt gtggccttct ttgagattgg tcctggcccc atccctggt | 1680 |
| tcattgtggc cgagctcttc agccagggcc cccgcccagc agccatggct gtagctggtt | 1740 |
| tctccaactg gacctgtaac ttcatcgttg catgggtttt ccagtatgtt gcggatgcta | 1800 |
| tgggtccta cgtcttcctt ctatttgccg tcctcctgct tggcttcttc atcttcacct | 1860 |
| tcctaagagt gcctgaaacc agaggccgga catttgacca gatctcggcc accttccgac | 1920 |
| ggacaccttc tctcttagag caggaggtga aacccagtac agaacttgaa tacttagggc | 1980 |
| cagatgagaa tgactaatcg atttgaagtg agacgctcca tcatctctct taattttttca | 2040 |
| tgactgacgt ttttttcttca tttttaattat catagtattt gtttgaaaaa aaaaaaaaaa | 2100 |
| aatttccctt atcaatgata tccttacgat tatataaatt ccttacctaa acctattatt | 2160 |
| tgtgtacata tatcagagta ttattacata tataacctttt ttctctaaaa caggaaaaaa | 2220 |
| aaaagaaaac gataacatgc tctgccatcc tttgttcacc gagcaaaatt aaaaacgcaa | 2280 |
| aatgaattgt ccctatgaaa ttattaaagg accacatcac cagacttatc tctgggggt | 2340 |
| cctctagaaa ataagtcagg tacttgcctg gactttcttc cagttg | 2386 |

<210> SEQ ID NO 11
<211> LENGTH: 7777
<212> TYPE: DNA
<213> ORGANISM: Homo sapiens

<400> SEQUENCE: 11

| | |
|---|---|
| atggagccca gcagcaagaa gctgacgggt cgcctcatgc tggctgtggg aggagcagtg | 60 |
| cttggctccc tgcagtttgg ctacaacact ggagtcatca tgccccccca gaaggtgatc | 120 |
| gaggagttct acaaccagac atgggtccac cgctatgggg agagcatcct gcccaccacg | 180 |
| ctcaccacgc tctggtccct ctcagtggcc atcttttctg ttgggggcat gattggctcc | 240 |
| ttctctgtgg gccttttcgt taaccgcttt ggccggcgga attcaatgct gatgatgaac | 300 |
| ctgctggcct tcgtgtccgc cgtgctcatg ggcttctcga aactgggcaa gtcctttgag | 360 |
| atgctgatcc tgggccgctt catcatcggt gtgtactgcg gcctgaccac aggcttcgtg | 420 |
| cccatgtatg tgggtgaagt gtcacccaca gcctttcgtg gggccctggg caccctgcac | 480 |
| cagctgggca tcgtcgtcgg catcctcatc gcccaggtgt tcggcctgga ctccatcatg | 540 |
| ggcaacaagg acctgtggcc cctgctgctg agcatcatct tcatcccggc cctgctgcag | 600 |
| tgcatcgtgc tgcccttctg ccccgagagt ccccgcttcc tgctcatcaa ccgcaacgag | 660 |
| gagaaccggg ccaagagtgt gctaaagaag ctgcgcggga cagctgacgt gaccatgac | 720 |
| ctgcaggaga tgaaggaaga gagtcggcag atgatgcggg agaagaaggt caccatcctg | 780 |
| gagctgttcc gctcccccgc ctaccgccag cccatcctca tcgctgtggt gctgcagctg | 840 |
| tcccagcagc tgtctggcat caacgctgtc ttctattact ccacgagcat cttcgagaag | 900 |
| gcgggggtgc agcagcctgt gtatgccacc attggctccg gtatcgtcaa cacggccttc | 960 |
| actgtcgtgt cgctgtttgt ggtggagcga gcaggccggc ggaccctgca cctcataggc | 1020 |
| ctcgctggca tggcggggtt gtgccatact catgaccatc gcgctagcact gctggagcag | 1080 |
| ctaccctgga tgtcctatct gagcatcgtg gccatctttg gctttgtggc cttctttgaa | 1140 |
| gtgggtcctg gccccatccc atggttcatc gtggctgaac tcttcagcca gggtccacgt | 1200 |
| ccagctgcca ttgccgttgc aggcttctcc aactggacct caaatttcat tgtgggcatg | 1260 |
| tgcttccagt atgtggagca actgtgtggt ccctacgtct tcatcatctt cactgtgctc | 1320 |
| ctggttctgt tcttcatctt cacctacttc aaagttcctg agactaaagg ccggaccttc | 1380 |

-continued

```
gatgagatcg cttccggctt ccggcagggg ggagccagcc aaagtgataa gacacccgag    1440
gagctgttcc atcccctggg ggctgattcc caagtgtgat aagcttatcg ataccgtcga    1500
cctcgagtca tgtaattagt tatgtcacgc ttacattcac gccctccccc cacatccgct    1560
ctaaccgaaa aggaaggagt tagacaacct gaagtctagg tccctattta ttttttttata   1620 gttatgttag tattaagaac gttatttata tttcaaattt ttcttttttt tctgtacaga    1680
cgcgtgtacg catgtaacat tatactgaaa accttgcttg agaaggtttt gggacgctcg    1740
aaggctttaa tttgcggccg gtacccaatt cgccctatag tgagtcgtat tacgcgcgct    1800
cactggccgt cgttttacaa cgtcgtgact gggaaaaccc tggcgttacc caacttaatc    1860
gccttgcagc acatcccct ttcgccagct ggcgtaatag cgaagaggcc cgcaccgatc     1920
gcccttccca acagttgcgc agcctgaatg gcgaatggcg cgacgcgccc tgtagcggcg    1980
cattaagcgc ggcgggtgtg gtggttacgc gcagcgtgac cgctacactt gccagcgccc    2040
tagcgcccgc tcctttcgct ttcttccctt cctttctcgc cacgttcgcc ggctttcccc    2100
gtcaagctct aaatcggggg ctccctttag ggttccgatt tagtgcttta cggcacctcg    2160
accccaaaaa acttgattag ggtgatggtt cacgtagtgg gccatcgccc tgatagacgg    2220
tttttcgccc tttgacgttg gagtccacgt tctttaatag tggactcttg ttccaaactg    2280
gaacaacact caaccctatc tcggtctatt cttttgattt ataagggatt ttgccgattt    2340
cggcctattg gttaaaaaat gagctgattt aacaaaaatt taacgcgaat tttaacaaaa    2400
tattaacgtt tacaatttcc tgatgcggta ttttctcctt acgcatctgt gcggtatttc    2460
acaccgcata gggtaataac tgatataatt aaattgaagc tctaatttgt gagtttagta    2520
tacatgcatt tacttataat acagtttttt agttttgctg gccgcatctt ctcaaatatg    2580
cttcccagcc tgcttttctg taacgttcac cctctacctt agcatccctt ccctttgcaa    2640
atagtcctct tccaacaata ataatgtcag atcctgtaga gaccacatca tccacggttc    2700
tatactgttg acccaatgcg tctcccttgt catctaaacc cacaccgggt gtcataatca    2760
accaatcgta accttcatct cttccaccca tgtctctttg agcaataaag ccgataacaa    2820
aatctttgtc gctcttcgca atgtcaacag taccttagt atattctcca gtagatagg     2880 agcccttgca tgacaattct gctaacatca aaaggcctct aggttccttt gttacttctt    2940
ctgccgcctg cttcaaaccg ctaacaatac ctgggcccac cacaccgtgt gcattcgtaa    3000
tgtctgccca ttctgctatt ctgtatacac ccgcagagta ctgcaatttg actgtattac    3060
caatgtcagc aaattttctg tcttcgaaga gtaaaaaatt gtacttggcg ataatgcct    3120 ttagcggctt aactgtgccc tccatggaaa atcagtcaa gatatccaca tgtgttttta    3180
gtaaacaaat tttgggacct aatgcttcaa ctaactccag taattccttg gtggtacgaa    3240
catccaatga agcacacaag tttgtttgct tttcgtgcat gatattaaat agcttggcag    3300
caacaggact aggatgagta gcagcacgtt ccttatatgt agctttcgac atgatttatc    3360
ttcgtttcct gcaggttttt gttctgtgca gttgggttaa gaatactggg caatttcatg    3420
tttcttcaac actacatatg cgtatatata ccaatctaag tctgtgctcc ttccttcgtt    3480
cttccttctg ttcggagatt accgaatcaa aaaatttca aagaaaccga atcaaaaaa     3540 aagaataaaa aaaaatgat gaattgaatt gaaaagctgt ggtatggtgc actctcagta    3600
caatctgctc tgatgccgca tagttaagcc agccccgaca cccgccaaca cccgctgacg    3660
cgccctgacg ggcttgtctg ctcccggcat ccgcttacag acaagctgtg accgtctccg    3720
```

```
ggagctgcat gtgtcagagg ttttcaccgt catcaccgaa acgcgcgaga cgaaagggcc    3780
tcgtgatacg cctattttta taggttaatg tcatgataat aatggtttct tagtatgatc    3840
caatatcaaa ggaaatgata gcattgaagg atgagactaa tccaattgag gagtggcagc    3900
atatagaaca gctaaagggt agtgctgaag gaagcatacg ataccccgca tggaatggga    3960
taatatcaca ggaggtacta gactacccttt catcctacat aaatagacgc atataagtac    4020
gcatttaagc ataaacacgc actatgccgt tcttctcatg tatatatata tacaggcaac    4080
acgcagatat aggtgcgacg tgaacagtga gctgtatgtg cgcagctcgc gttgcatttt    4140
cggaagcgct cgttttcgga aacgctttga agttcctatt ccgaagttcc tattctctag    4200
aaagtatagg aacttcagag cgcttttgaa accaaaagc gctctgaaga cgcactttca     4260 aaaaccaaa aacgcaccgg actgtaacga gctactaaaa tattgcgaat accgcttcca     4320
caaacattgc tcaaaagtat ctctttgcta tatatctctg tgctatatcc ctatataacc    4380
tacccatcca ccttttcgctc cttgaacttg catctaaact cgacctctac atttttttatg  4440 tttatctcta gtattactct ttagacaaaa aaattgtagt aagaactatt catagagtga    4500
atcgaaaaca atacgaaaat gtaaacattt cctatacgta gtatatagag acaaaataga    4560
agaaaccgtt cataattttc tgaccaatga agaatcatca acgctatcac tttctgttca    4620
caaagtatgc gcaatccaca tcggtataga atataatcgg ggatgccttt atcttgaaaa    4680
aatgcacccg cagcttcgct agtaatcagt aaacgcggga agtggagtca ggctttttttt  4740 atggaagaga aaatagacac caaagtagcc ttcttctaac cttaacggac ctacagtgca    4800
aaaagttatc aagagactgc attatagagc gcacaaagga gaaaaaaagt aatctaagat    4860
gctttgttag aaaaatagcg ctctcgggat gcattttgt agaacaaaaaa agaagtatag    4920 attctttgtt ggtaaaatag cgctctcgcg ttgcatttct gttctgtaaa aatgcagctc    4980
agattctttg tttgaaaaat tagcgctctc gcgttgcatt tttgttttac aaaaatgaag    5040
cacagattct tcgttggtaa aatagcgctt tcgcgttgca tttctgttct gtaaaaatgc    5100
agctcagatt ctttgtttga aaattagcg ctctcgcgtt gcattttgt tctacaaaat     5160 gaagcacaga tgcttcgttc aggtggcact tttcgggaa atgtgcgcgg aaccctatt     5220 tgtttattt tctaaataca ttcaaatatg tatccgctca tgagacaata accctgataa    5280
atgcttcaat aatattgaaa aaggaagagt atgagtattc aacatttccg tgtcgccctt    5340
attccctttt ttgcggcatt ttgccttcct gttttttgctc acccagaaac gctggtgaaa    5400
gtaaaagatg ctgaagatca gttgggtgca cgagtgggtt acatcgaact ggatctcaac    5460
agcggtaaga tccttgagag ttttcgcccc gaagaacgtt ttccaatgat gagcactttt    5520
aaagttctgc tatgtggcgc ggtattatcc cgtattgacg ccgggcaaga gcaactcggt    5580
cgccgcatac actattctca gaatgacttg gttgagtact caccagtcac agaaaagcat    5640
cttacggatg gcatgacagt aagagaatta tgcagtgctg ccataaccat gagtgataac    5700
actgcggcca acttacttct gacaacgatc ggaggaccga aggagctaac cgcttttttg    5760
cacaacatgg gggatcatgt aactcgcctt gatcgttggg aaccggagct gaatgaagcc    5820
ataccaaacg acgagcgtga caccacgatg cctgtagcaa tggcaacaac gttgcgcaaa    5880
ctattaactg gcgaactact tactctagct tcccggcaac aattaataga ctggatggag    5940
gcggataaag ttgcaggacc acttctgcgc tcggcccttc cggctggctg gtttattgct    6000
gataaatctg gagccggtga gcgtgggtct cgcggtatca ttgcagcact ggggccagat    6060
ggtaagccct cccgtatcgt agttatctac acgacgggga gtcaggcaac tatggatgaa    6120
```

-continued

```
cgaaatagac agatcgctga gataggtgcc tcactgatta agcattggta actgtcagac    6180
caagtttact catatatact ttagattgat ttaaaacttc attttttaatt taaaaggatc    6240
taggtgaaga tccttttttga taatctcatg accaaaatcc cttaacgtga gttttcgttc    6300
cactgagcgt cagaccccgt agaaaagatc aaaggatctt cttgagatcc ttttttttctg    6360
cgcgtaatct gctgcttgca acaaaaaaaa ccaccgctac cagcggtggt ttgtttgccg    6420
gatcaagagc taccaactct ttttccgaag gtaactggct tcagcagagc gcagatacca    6480
aatactgtcc ttctagtgta gccgtagtta ggccaccact tcaagaactc tgtagcaccg    6540
cctacatacc tcgctctgct aatcctgtta ccagtggctg ctgccagtgg cgataagtcg    6600
tgtcttaccg ggttggactc aagacgatag ttaccggata aggcgcagcg gtcgggctga    6660
acggggggtt cgtgcacaca gcccagcttg gagcgaacga cctacaccga actgagatac    6720
ctacagcgtg agctatgaga aagcgccacg cttcccgaag ggagaaaggc ggacaggtat    6780
ccggtaagcg gcagggtcgg aacaggagag cgcacgaggg agcttccagg gggaaacgcc    6840
tggtatcttt atagtcctgt cgggtttcgc caccctctgac ttgagcgtcg attttttgtga    6900
tgctcgtcag gggggcggag cctatggaaa aacgccagca acgcggcctt tttacggttc    6960
ctggccttttt gctggccttt tgctcacatg ttctttcctg cgttatcccc tgattctgtg    7020
gataaccgta ttaccgcctt tgagtgagct gataccgctc gccgcagccg aacgaccgag    7080
cgcagcgagt cagtgagcga ggaagcggaa gagcgcccaa tacgcaaacc gcctctcccc    7140
gcgcgttggc cgattcatta atgcagctgg cacgacaggt ttcccgactg gaaagcgggc    7200
agtgagcgca acgcaattaa tgtgagttac ctcactcatt aggcacccca ggctttacac    7260
tttatgcttc cggctcctat gttgtgtgga attgtgagcg gataacaatt tcacacagga    7320
aacagctatg accatgatta cgccaagcgc gcaattaacc ctcactaaag ggaacaaaag    7380
ctggagctcg taggaacaat ttcgggcccc tgcgtgttct tctgaggttc atctttttaca    7440
tttgcttctg ctggataatt ttcagaggca acaaggaaaa attagatggc aaaaagtcgt    7500
cttttcaagga aaaatcccca ccatctttcg agatcccctg taacttattg gcaactgaaa    7560
gaatgaaaag gaggaaaata caaaatatac tagaactgaa aaaaaaaaag tataaataga    7620
gacgatatat gccaatactt cacaatgttc gaatctattc ttcatttgca gctattgtaa    7680
aataataaaa catcaagaac aaacaagctc aacttgtctt ttctaagaac aaagaataaa    7740
cacaaaaaca aaaagttttt ttaattttaa tcaaaaa                            7777
```

<210> SEQ ID NO 12
<211> LENGTH: 2338
<212> TYPE: DNA
<213> ORGANISM: Rattus norvegicus

<400> SEQUENCE: 12

```
tcgactctag aggatcccct taagctaatc cttatgaatc cggagaaaag cggggtcttt     60
taactcaata aaattttccg aaatccttttt tcctacgcgt tttcttcggg aactagatag    120
gtggctcttc cacctgtttt tccatcattt tagttttttcg caagccatgc gtgccttttc    180
gtttttttgcga tggcgaacga gggctggaaa aattaacggt acgccgccta acgatagtaa    240
taggccacgc aactggcgtg gacgacaaca ataagtcgcc cattttttat gttttcaaaa    300
cctagcaacc cccaccaaac ttgtcatcgt tcccggattc acaaatgata taaaaagcga    360
ttacaattct acattctaac cagatttgag atttcctctt tctcaattcc tcttatatta    420
```

-continued

| | |
|---|---|
| gattataaga acaacaaatt aaattacaaa aagacttata aagcaacata atgtctgaat | 480 |
| tcagcaagaa ggtgacgggc cgccttatgt tggccgtggg agggcagtg ctcggatccc | 540 |
| tgcagttcgg ctataacacc ggtgtcatca acgcccccca aaggtaatt gaggagttct | 600 |
| acaatcaaac atggaaccac cgctatggag agtccatccc atccaccaca ctcaccacac | 660 |
| tctggtctct ctccgtggcc atcttctctg tcgggggcat gattggttcc ttctctgtgg | 720 |
| gcctctttgt taatcgcttt ggcaggcgga actccatgct gatgatgaac ctgttggcct | 780 |
| ttgtgtctgc cgtgcttatg ggtttctcca aactgggcaa gtcctttgag atgctgatcc | 840 |
| tgggccgctt catcattgga gtgtactgtg gcctgaccac cggctttgtg cccatgtatg | 900 |
| tgggggaggt gtcacccaca gctcttcgtg gagccctggg caccctgcac cagctgggca | 960 |
| tcgtcgttgg gatccttatt gcccaggtgt tcggcttaga ctccatcatg ggcaatgcag | 1020 |
| acttgtggcc tctactgctc agtgtcatct tcatcccagc cctgctacag tgtatcctgt | 1080 |
| tgcccttctg ccctgagagc cccgcttcc tgctcatcaa tcgtaacgag gagaaccggg | 1140 |
| ccaagagtgt gctgaaaaag cttcgaggga cagccgatgt gacccgagac ctgcaggaga | 1200 |
| tgaaagaaga gggtcggcag atgatgcggg agaagaaggt caccatcttg gagctgttcc | 1260 |
| gctcacccgc ctaccgccag cccatcctca tcgccgtggt gctgcagctg tcccagcagc | 1320 |
| tgtcgggcat caatgctgtg ttctactact caacgagcat cttcgagaag caggtgtgc | 1380 |
| agcagcctgt gtatgccacc atcggctcgg gtatcgtcaa cacggccttc actgtggtgt | 1440 |
| cgctgttcgt cgtggagcga gctggccgtc ggacccctgca tctcattggt ctggctggca | 1500 |
| tggcgggctg tgctgtgctc atgaccatcg ccctggccct gctggagcag ctgccctgga | 1560 |
| tgtcctatct gagtatcgtg gccatctttg gctttgtggc cttctttgaa gtaggccctg | 1620 |
| gtcctattcc atggttcatt gtggccgagc tgttcagcca ggggccccga cctgctgctg | 1680 |
| ttgctgtggc tggcttctct aactggacct caaacttcat cgtgggcatg tgcttccaat | 1740 |
| atgtggagca actgtgtggc ccctacgtct tcatcatctt cacggtgctg ctggtactct | 1800 |
| tcttcatctt cacctacttc aaagttcctg agaccaaagg ccggaccttc gatgagatcg | 1860 |
| cttccggctt ccggcagggg ggtgccagcc agagcgacaa gacacctgag gagctcttcc | 1920 |
| accctctggg ggctgactcc caagtgtaat cgatttgaag tgagacgctc catcatctct | 1980 |
| cttaattttt catgactgac gttttttctt cattttaatt atcatagtat ttgtttgaaa | 2040 |
| aaaaaaaaaa aaaatttccc ttatcaatga tatccttacg attatataaa ttccttacct | 2100 |
| aaacctatta tttgtgtaca tatatcagag tattattaca tatataacct ttttctctaa | 2160 |
| aacaggaaaa aaaaagaaa acgataacat gctctgccat cctttgttca ccgagcaaaa | 2220 |
| ttaaaaacgc aaaatgaatt gtccctatga aattattaaa ggaccacatc accagactta | 2280 |
| tctctggggg gtcctctaga aaataagtca ggtacttgcc tggactttct tccagttg | 2338 |

<210> SEQ ID NO 13
<211> LENGTH: 2338
<212> TYPE: DNA
<213> ORGANISM: Rattus norvegicus

<400> SEQUENCE: 13

| | |
|---|---|
| tcgactctag aggatcccct taagctaatc cttatgaatc cggagaaaag cggggtcttt | 60 |
| taactcaata aaattttccg aaatcctttt tcctacgcgt tttcttcggg aactagatag | 120 |
| gtggctcttc cacctgtttt tccatcattt tagttttttcg caagccatgc gtgccttttc | 180 |
| gttttttgcga tggcgaacga gggctggaaa aattaacggt acgccgccta acgatagtaa | 240 |

-continued

```
taggccacgc aactggcgtg gacgacaaca ataagtcgcc cattttttat gttttcaaaa     300
cctagcaacc cccaccaaac ttgtcatcgt tcccggattc acaaatgata taaaaagcga     360
ttacaattct acattctaac cagatttgag atttcctctt tctcaattcc tcttatatta     420
gattataaga acaacaaatt aaattacaaa aagacttata aagcaacata atgtctgaat     480
tcagcaagaa ggtgacgggc cgccttatgt tggccgtggg aggggcagtg ctcggatccc     540
tgcagttcgg ctataacacc ggtgtcatca acgccccca gaaggtaatt gaggagttct     600
acaatcaaac atggaaccac cgctatggag agtccatccc atccaccaca ctcaccacac     660
tctggtctct ctccatggcc atcttctctg tcggggcat gattggttcc ttctctgtgg     720
gcctctttgt taatcgcttt ggcaggcgga actccatgct gatgatgaac ctgttggcct     780
ttgtgtctgc cgtgcttatg ggtttctcca actgggcaa gtcctttgag atgctgatcc     840
tgggccgctt catcattgga gtgtactgtg gcctgaccac cggctttgtg cccatgtatg     900
tgggggaggt gtcacccaca gctcttcgtg gagccctggg cacctgcac cagctgggca     960 tcgtcgttgg gatccttatt gcccaggtgt tcggcttaga ctccatcatg ggcaatgcag    1020
acttgtggcc tctactgctc agtgtcatct tcatcccagc cctgctacag tgtatcctgt    1080
tgcccttctg ccctgagagc cccgcttcc tgctcatcaa tcgtaacgag gagaaccggg    1140
ccaagagtgt gctgaaaaag cttcgaggga cagccgatgt gacccgagac ctgcaggaga    1200
tgaaagaaga gggtcggcag atgatgcggg agaagaaggt caccatcttg gagctgttcc    1260
gctcacccgc ctaccgccag cccatcctca tcgccgtggt gctgcagctg tcccagcagc    1320
tgtcgggcat caatgctgtg ttctactact caacgagcat cttcgagaag gcaggtgtgc    1380
agcagcctgt gtatgccacc atcggctcgg gtatcgtcaa cacggccttc actgtggtgt    1440
cgctgttcgt cgtggagcga gctggccgtc ggaccctgca tctcattggt ctggctggca    1500
tggcgggctg tgctgtgctc atgaccatcg ccctggccct gctggagcag ctgccctgga    1560
tgtcctatct gagtatcgtg gccatctttg gctttgtggc cttctttgaa gtaggccctg    1620
gtcctattcc atggttcatt gtggccgagc tgttcagcca ggggccccga cctgctgctg    1680
ttgctgtggc tggcttctct aactggacct caaacttcat cgtgggcatg tgcttccaat    1740
atgtggagca actgtgtggc ccctacgtct tcatcatctt cacggtgctg ctggtactct    1800
tcttcatctt cacctacttc aaagttcctg agaccaaagg ccggaccttc gatgagatcg    1860
cttccggctt ccggcagggg ggtgccagcc agagcgacaa gacacctgag gagctcttcc    1920
accctctggg ggctgactcc caagtgtaat cgatttgaag tgagacgctc catcatctct    1980
cttaattttt catgactgac gttttttctt catttttaat atcatagtat ttgtttgaaa    2040
aaaaaaaaaa aaaatttccc ttatcaatga tatccttacg attatataaa ttccttacct    2100
aaacctatta tttgtgtaca tatatcagag tattattaca tatataacct tttctctaa    2160 aacaggaaaa aaaaagaaa acgataacat gctctgccat cctttgttca ccgagcaaaa    2220
ttaaaaacgc aaaatgaatt gtccctatga aattattaaa ggaccacatc accagactta    2280
tctctggggg gtcctctaga aaataagtca ggtacttgcc tggactttct tccagttg     2338
```

<210> SEQ ID NO 14
<211> LENGTH: 2338
<212> TYPE: DNA
<213> ORGANISM: Rattus norvegicus

<400> SEQUENCE: 14

-continued

```
tcgactctag aggatcccct taagctaatc cttatgaatc cggagaaaag cggggtcttt      60
taactcaata aaattttccg aaatccttt tcctacgcgt tttcttcggg aactagatag      120
gtggctcttc cacctgtttt tccatcattt tagtttttcg caagccatgc gtgccttttc     180
gttttttgcga tggcgaacga gggctggaaa aattaacggt acgccgccta acgatagtaa   240
taggccacgc aactggcgtg gacgacaaca ataagtcgcc catttttat gttttcaaaa     300
cctagcaacc cccaccaaac ttgtcatcgt tcccggattc acaaatgata taaaaagcga    360
ttacaattct acattctaac cagatttgag atttcctctt tctcaattcc tcttatatta    420
gattataaga acaacaaatt aaattacaaa aagacttata aagcaacata atgtctgaat    480
tcagcaagaa ggtgacgggc cgccttatgt tggccgtggg aggggcagtg ctcggatccc    540
tgcagttcgg ctataacacc ggtgtcatca acgcccccca gaaggtaatt gaggagttct    600
acaatcaaac atggaaccac cgctatggag agtccatccc atccaccaca ctcaccacac    660
tctggtctct ctccgtgatg atcttctctg tcggggcat gattggttcc ttctctgtgg     720
gcctctttgt taatcgcttt ggcaggcgga actccatgct gatgatgaac ctgttggcct    780
ttgtgtctgc cgtgcttatg ggtttctcca aactgggcaa gtcctttgag atgctgatcc    840
tgggccgctt catcattgga gtgtactgtg gcctgaccac cggctttgtg cccatgtatg    900
tgggggaggt gtcacccaca gctcttcgtg gagccctggg caccctgcac cagctgggca    960
tcgtcgttgg gatccttatt gcccaggtgt tcggcttaga ctccatcatg ggcaatgcag   1020
acttgtggcc tctactgctc agtgtcatct tcatcccagc cctgctacag tgtatcctgt   1080
tgcccttctg ccctgagagc ccccgcttcc tgctcatcaa tcgtaacgag gagaaccggg   1140
ccaagagtgt gctgaaaaag cttcgaggga cagccgatgt gacccgagac ctgcaggaga   1200
tgaaagaaga gggtcggcag atgatgcggg agaagaaggt caccatcttg gagctgttcc   1260
gctcacccgc ctaccgccag cccatcctca tcgccgtggt gctgcagctg tcccagcagc   1320
tgtcgggcat caatgctgtg ttctactact caacgagcat cttcgagaag gcaggtgtgc   1380
agcagcctgt gtatgccacc atcggctcgg gtatcgtcaa cacggccttc actgtggtgt   1440
cgctgttcgt cgtggagcga gctggccgtc ggaccctgca tctcattggt ctggctggca   1500
tggcgggctg tgctgtgctc atgaccatcg ccctggccct gctggagcag ctgccctgga   1560
tgtcctatct gagtatcgtg gccatctttg gctttgtggc cttctttgaa gtaggccctg   1620
gtcctattcc atggttcatt gtggccgagc tgttcagcca ggggccccga cctgctgctg   1680
ttgctgtggc tggcttctct aactggacct caaacttcat cgtgggcatg tgcttccaat   1740
atgtggagca actgtgtggc ccctacgtct tcatcatctt cacggtgctg ctggtactct   1800
tcttcatctt cacctacttc aaagttcctg agaccaaagg ccggaccttc gatgagatcg   1860
cttccggctt ccggcagggg ggtgccagcc agagcgacaa gacacctgag gagctcttcc   1920
accctctggg ggctgactcc caagtgtaat cgatttgaag tgagacgctc catcatctct   1980
cttaattttt catgactgac gttttttctt catttaatt atcatagtat ttgtttgaaa    2040
aaaaaaaaaa aaatttccc ttatcaatga tatccttacg attatataaa ttccttacct    2100
aaacctatta tttgtgtaca tatatcagag tattattaca tatataacct ttttctctaa   2160
aacaggaaaa aaaaagaaa acgataacat gctctgccat cctttgttca ccgagcaaaa    2220
ttaaaaacgc aaaatgaatt gtccctatga aattattaaa ggaccacatc accagactta   2280
tctctggggg gtcctctaga aaataagtca ggtacttgcc tggactttct tccagttg     2338
```

<210> SEQ ID NO 15
<211> LENGTH: 6360
<212> TYPE: DNA
<213> ORGANISM: Artificial Sequence
<220> FEATURE:
<223> OTHER INFORMATION: Vector

<400> SEQUENCE: 15

| | | | | | |
|---|---|---|---|---|---|
| cgtaggaaca | atttcgggcc | cctgcgtgtt | cttctgaggt | tcatctttta | catttgcttc | 60 |
| tgctggataa | ttttcagagg | caacaaggaa | aaattagatg | gcaaaaagtc | gtctttcaag | 120 |
| gaaaaatccc | caccatcttt | cgagatcccc | tgtaacttat | tggcaactga | agaatgaaa | 180 |
| aggaggaaaa | tacaaaatat | actagaactg | aaaaaaaaaa | agtataaata | gagacgatat | 240 |
| atgccaatac | ttcacaatgt | tcgaatctat | tcttcatttg | cagctattgt | aaaataataa | 300 |
| aacatcaaga | acaaacaagc | tcaacttgtc | ttttctaaga | acaaagaata | aacacaaaaa | 360 |
| caaaaagttt | ttttaatttt | aatcaaaaag | ttaacatgca | tcaccatcac | catcacacta | 420 |
| gtggatcccc | cgggctgcag | gaattcgata | tcaagcttat | cgataccgtc | gacctcgagt | 480 |
| catgtaatta | gttatgtcac | gcttacattc | acgccctccc | cccacatccg | ctctaaccga | 540 |
| aaaggaagga | gttagacaac | ctgaagtcta | ggtcccctatt | tattttttta | tagttatgtt | 600 |
| agtattaaga | acgttattta | tatttcaaat | ttttctttt | tttctgtaca | gacgcgtgta | 660 |
| cgcatgtaac | attatactga | aaaccttgct | tgagaaggtt | tgggacgct | cgaaggcttt | 720 |
| aatttgcggc | cggtacccaa | ttcgccctat | agtgagtcgt | attacgcgcg | ctcactggcc | 780 |
| gtcgttttac | aacgtcgtga | ctgggaaaac | cctggcgtta | cccaacttaa | tcgccttgca | 840 |
| gcacatcccc | ctttcgccag | ctggcgtaat | agcgaagagg | cccgcaccga | tcgcccttcc | 900 |
| caacagttgc | gcagcctgaa | tggcgaatgg | cgcgacgcgc | cctgtagcgg | cgcattaagc | 960 |
| gcggcgggtg | tggtggttac | gcgcagcgtg | accgctacac | ttgccagcgc | cctagcgccc | 1020 |
| gctcctttcg | ctttcttccc | ttcctttctc | gccacgttcg | ccggctttcc | ccgtcaagct | 1080 |
| ctaaatcggg | ggctcccttt | agggttccga | tttagtgctt | tacggcacct | cgaccccaaa | 1140 |
| aaacttgatt | agggtgatgg | ttcacgtagt | gggccatcgc | cctgatagac | ggttttcgc | 1200 |
| cctttgacgt | tggagtccac | gttctttaat | agtggactct | tgttccaaac | tggaacaaca | 1260 |
| ctcaacccta | tctcggtcta | ttcttttgat | ttataaggga | ttttgccgat | tcggcctat | 1320 |
| tggttaaaaa | atgagctgat | ttaacaaaaa | tttaacgcga | attttaacaa | aatattaacg | 1380 |
| tttacaattt | cctgatgcgg | tattttctcc | ttacgcatct | gtgcggtatt | tcacaccgca | 1440 |
| tagggtaata | actgatataa | ttaaattgaa | gctctaattt | gtgagtttag | tatacatgca | 1500 |
| tttacttata | atacagtttt | ttagttttgc | tggccgcatc | ttctcaaata | tgcttcccag | 1560 |
| cctgctttc | tgtaacgttc | accctctacc | ttagcatccc | ttccctttgc | aaatagtcct | 1620 |
| cttccaacaa | taataatgtc | agatcctgta | gagaccacat | catccacggt | tctatactgt | 1680 |
| tgacccaatg | cgtctccctt | gtcatctaaa | cccacaccgg | gtgtcataat | caaccaatcg | 1740 |
| taaccttcat | ctcttccacc | catgtctctt | gagcaataa | agccgataac | aaaatctttg | 1800 |
| tcgctcttcg | caatgtcaac | agtacccta | gtatattctc | cagtagatag | ggagcccttg | 1860 |
| catgacaatt | ctgctaacat | caaaaggcct | ctaggttcct | tgttacttc | ttctgccgcc | 1920 |
| tgcttcaaac | cgctaacaat | acctgggccc | accacaccgt | gtgcattcgt | aatgtctgcc | 1980 |
| cattctgcta | ttctgtatac | acccgcagag | tactgcaatt | tgactgtatt | accaatgtca | 2040 |
| gcaaattttc | tgtcttcgaa | gagtaaaaaa | ttgtacttgg | cggataatgc | ctttagcggc | 2100 |

-continued

```
ttaactgtgc cctccatgga aaaatcagtc aagatatcca catgtgtttt tagtaaacaa    2160
attttgggac ctaatgcttc aactaactcc agtaattcct tggtggtacg aacatccaat    2220
gaagcacaca agtttgtttg cttttcgtgc atgatattaa atagcttggc agcaacagga    2280
ctaggatgag tagcagcacg ttccttatat gtagctttcg acatgattta tcttcgtttc    2340
ctgcaggttt ttgttctgtg cagttgggtt aagaatactg ggcaatttca tgtttcttca    2400
acactacata tgcgtatata taccaatcta agtctgtgct ccttccttcg ttcttccttc    2460
tgttcggaga ttaccgaatc aaaaaaattt caaagaaacc gaaatcaaaa aaagaataa     2520 aaaaaaaatg atgaattgaa ttgaaaagct gtggtatggt gcactctcag tacaatctgc    2580
tctgatgccg catagttaag ccagccccga cacccgccaa cacccgctga cgcgccctga    2640
cgggcttgtc tgctcccggc atccgcttac agacaagctg tgaccgtctc cgggagctgc    2700
atgtgtcaga ggttttcacc gtcatcaccg aaacgcgcga gacgaaaggg cctcgtgata    2760
cgcctatttt tataggttaa tgtcatgata ataatggttt cttagtatga tccaatatca    2820
aaggaaatga tagcattgaa ggatgagact aatccaattg aggagtggca gcatatagaa    2880
cagctaaagg gtagtgctga aggaagcata cgatacccg catggaatgg gataatatca     2940
caggaggtac tagactacct ttcatcctac ataaatagac gcatataagt acgcatttaa    3000
gcataaacac gcactatgcc gttcttctca tgtatatata tatacaggca acacgcagat    3060
ataggtgcga cgtgaacagt gagctgtatg tgcgcagctc gcgttgcatt tcggaagcg     3120 ctcgttttcg gaaacgcttt gaagttccta ttccgaagtt cctattctct agaaagtata    3180
ggaacttcag agcgcttttg aaaaccaaaa gcgctctgaa gacgcacttt caaaaaacca    3240
aaaacgcacc ggactgtaac gagctactaa aatattgcga ataccgcttc cacaaacatt    3300
gctcaaaagt atctctttgc tatatatctc tgtgctatat ccctatataa cctacccatc    3360 caccttttcgc tccttgaact tgcatctaaa ctcgacctct acatttttta tgtttatctc    3420
tagtattact ctttagacaa aaaaattgta gtaagaacta ttcatagagt gaatcgaaaa    3480
caatacgaaa atgtaaacat ttcctatacg tagtatatag agacaaaata gaagaaaccg    3540
ttcataattt tctgaccaat gaagaatcat caacgctatc actttctgtt cacaaagtat    3600
gcgcaatcca catcggtata gaatataatc ggggatgcct ttatcttgaa aaaatgcacc    3660
cgcagcttcg ctagtaatca gtaaacgcgg gaagtggagt caggcttttt ttatggaaga    3720
gaaaatagac accaaagtag ccttcttcta accttaacgg acctacagtg caaaaagtta    3780
tcaagagact gcattataga gcgcacaaag gagaaaaaaa gtaatctaag atgctttgtt    3840
agaaaaatag cgctctcggg atgcattttt gtagaacaaa aaagaagtat agattctttg    3900
ttggtaaaat agcgctctcg cgttgcattt ctgttctgta aaaatgcagc tcagattctt    3960
tgtttgaaaa attagcgctc tcgcgttgca ttttttgtttt acaaaatga agcacagatt    4020 cttcgttggt aaaatagcgc tttcgcgttg catttctgtt ctgtaaaaat gcagctcaga    4080
ttctttgttt gaaaaattag cgctctcgcg ttgcattttt gttctacaaa atgaagcaca    4140
gatgcttcgt tcaggtggca cttttcgggg aaatgtgcgc ggaacccta tttgtttatt     4200 tttctaaata cattcaaata tgtatccgct catgagacaa taaccctgat aaatgcttca    4260
ataatattga aaaaggaaga gtatgagtat tcaacatttc cgtgtcgccc ttattccctt    4320
ttttgcggca ttttgccttc ctgttttttgc tcacccagaa acgctggtga agtaaaaga    4380 tgctgaagat cagttgggtg cacgagtggg ttacatcgaa ctggatctca acagcggtaa    4440
gatccttgag agttttcgcc ccgaagaacg ttttccaatg atgagcactt taaagttct     4500
```

-continued

```
gctatgtggc gcggtattat cccgtattga cgccgggcaa gagcaactcg gtcgccgcat    4560
acactattct cagaatgact tggttgagta ctcaccagtc acagaaaagc atcttacgga    4620
tggcatgaca gtaagagaat tatgcagtgc tgccataacc atgagtgata acactgcggc    4680
caacttactt ctgacaacga tcggaggacc gaaggagcta accgcttttt tgcacaacat    4740
gggggatcat gtaactcgcc ttgatcgttg ggaaccggag ctgaatgaag ccataccaaa    4800
cgacgagcgt gacaccacga tgcctgtagc aatggcaaca acgttgcgca aactattaac    4860
tggcgaacta cttactctag cttcccggca acaattaata gactggatgg aggcggataa    4920
agttgcagga ccacttctgc gctcggccct tccggctggc tggtttattg ctgataaatc    4980
tggagccggt gagcgtgggt ctcgcggtat cattgcagca ctggggccag atggtaagcc    5040
ctcccgtatc gtagttatct acacgacggg gagtcaggca actatggatg aacgaaatag    5100
acagatcgct gagataggtg cctcactgat taagcattgg taactgtcag accaagttta    5160
ctcatatata ctttagattg atttaaaact tcatttttaa tttaaaagga tctaggtgaa    5220 gatcctttt gataatctca tgaccaaaat cccttaacgt gagttttcgt tccactgagc    5280
gtcagacccc gtagaaaaga tcaaaggatc ttcttgagat cctttttttc tgcgcgtaat    5340
ctgctgcttg caaacaaaaa aaccaccgct accagcggtg gtttgtttgc cggatcaaga    5400
gctaccaact ctttttccga aggtaactgg cttcagcaga gcgcagatac caaatactgt    5460
ccttctagtg tagccgtagt taggccacca cttcaagaac tctgtagcac cgcctacata    5520
cctcgctctg ctaatcctgt taccagtggc tgctgccagt ggcgataagt cgtgtcttac    5580
cgggttggac tcaagacgat agttaccgga taaggcgcag cggtcgggct gaacggggggg   5640 ttcgtgcaca gcccagct tggagcgaac gacctacacc gaactgagat acctacagcg    5700
tgagctatga gaaagcgcca cgcttcccga agggagaaag gcggacaggt atccggtaag   5760
cggcagggtc ggaacaggag agcgcacgag ggagcttcca gggggaaacg cctggtatct    5820
ttatagtcct gtcgggtttc gccacctctg acttgagcgt cgatttttgt gatgctcgtc    5880 agggggggcgg agcctatgga aaaacgccag caacgcggcc ttttttacggt tcctggcctt    5940 ttgctggcct tttgctcaca tgttctttcc tgcgttatcc cctgattctg tggataaccg    6000
tattaccgcc tttgagtgag ctgataccgc tcgccgcagc cgaacgaccg agcgcagcga    6060
gtcagtgagc gaggaagcgg aagagcgccc aatacgcaaa ccgcctctcc ccgcgcgttg    6120
gccgattcat taatgcagct ggcacgacag gtttcccgac tggaaagcgg gcagtgagcg    6180
caacgcaatt aatgtgagtt acctcactca ttaggcaccc caggctttac actttatgct    6240
tccggctcct atgttgtgtg gaattgtgag cggataacaa tttcacacag gaaacagcta    6300
tgaccatgat tacgccaagc gcgcaattaa ccctcactaa agggaacaaa agctggagct    6360
```

```
<210> SEQ ID NO 16
<211> LENGTH: 24
<212> TYPE: DNA
<213> ORGANISM: Rattus norvegicus

<400> SEQUENCE: 16
ctttctcaat tcctcttata ttag                                             24

<210> SEQ ID NO 17
<211> LENGTH: 36
<212> TYPE: DNA
<213> ORGANISM: Rattus norvegicus
```

-continued

```
<400> SEQUENCE: 17
cccgacagag aagatcatca cggagagaga ccagag                    36

<210> SEQ ID NO 18
<211> LENGTH: 24
<212> TYPE: DNA
<213> ORGANISM: Rattus norvegicus

<400> SEQUENCE: 18
aacgtcagtc atgaaaaatt aaga                                 24
```